United States Patent
Kidron

(10) Patent No.: US 10,398,762 B2
(45) Date of Patent: Sep. 3, 2019

(54) METHODS AND COMPOSITIONS FOR TREATING DIABETES

(71) Applicant: Oramed Ltd., Jerusalem (IL)

(72) Inventor: Miriam Kidron, Jerusalem (IL)

(73) Assignee: Oramed Ltd., Jerusalem (IL)

( * ) Notice: Subject to any disclaimer, the term of this patent is extended or adjusted under 35 U.S.C. 154(b) by 304 days.

(21) Appl. No.: 14/370,452

(22) PCT Filed: Jan. 3, 2013

(86) PCT No.: PCT/IL2013/050007
§ 371 (c)(1),
(2) Date: Jul. 2, 2014

(87) PCT Pub. No.: WO2013/102899
PCT Pub. Date: Jul. 11, 2013

(65) Prior Publication Data
US 2015/0017238 A1   Jan. 15, 2015

Related U.S. Application Data

(60) Provisional application No. 61/631,339, filed on Jan. 3, 2012.

(51) Int. Cl.
| | |
|---|---|
| *A61K 38/28* | (2006.01) |
| *A61K 38/26* | (2006.01) |
| *A61K 38/55* | (2006.01) |
| *A61K 45/06* | (2006.01) |
| *A61K 31/198* | (2006.01) |
| *A61K 9/48* | (2006.01) |
| *A61K 38/56* | (2006.01) |
| *A61K 38/57* | (2006.01) |
| *A61K 9/50* | (2006.01) |

(52) U.S. Cl.
CPC ............ *A61K 38/28* (2013.01); *A61K 9/4808* (2013.01); *A61K 9/4875* (2013.01); *A61K 9/4891* (2013.01); *A61K 31/198* (2013.01); *A61K 38/26* (2013.01); *A61K 38/55* (2013.01); *A61K 38/56* (2013.01); *A61K 38/57* (2013.01); *A61K 45/06* (2013.01); *A61K 9/5005* (2013.01)

(58) Field of Classification Search
CPC ........ A61K 38/26; A61K 38/57; A61K 38/55; A61K 38/56; A61K 9/4875; A61K 9/4808; A61K 9/4891; A61K 9/5005; A61K 38/28; A61K 31/198; A61K 45/06
See application file for complete search history.

(56) References Cited

U.S. PATENT DOCUMENTS

| | | |
|---|---|---|
| 4,579,730 A | 4/1986 | Kidron et al. |
| 5,034,415 A | 7/1991 | Rubin |
| 5,206,219 A | 4/1993 | Desai |
| 5,665,700 A | 9/1997 | Cho et al. |
| 5,824,638 A | 10/1998 | Burnside et al. |
| 6,692,766 B1 | 2/2004 | Rubinstein et al. |
| 6,761,903 B2 | 7/2004 | Chen et al. |
| 6,858,576 B1 | 2/2005 | Young et al. |
| 7,404,973 B2 | 7/2008 | Konwinski et al. |
| 9,186,412 B2 | 11/2015 | Kidron et al. |
| 9,259,456 B2 | 2/2016 | Kidron |
| 2002/0032171 A1 | 3/2002 | Chen et al. |
| 2003/0118610 A1 | 6/2003 | Stern et al. |
| 2004/0097410 A1 | 5/2004 | Zheng et al. |
| 2005/0143303 A1 | 6/2005 | Quay et al. |
| 2005/0232981 A1 | 10/2005 | Ben-Sasson |
| 2006/0018874 A1 | 1/2006 | Radhakrishnan et al. |
| 2006/0045868 A1* | 3/2006 | Meezan ............... A61K 9/0043 424/85.4 |
| 2006/0045869 A1 | 3/2006 | Meezan et al. |
| 2006/0234913 A1 | 10/2006 | Arbit et al. |
| 2006/0264401 A1 | 11/2006 | Campbell et al. |
| 2006/0286129 A1 | 12/2006 | Sarubbi |
| 2006/0293232 A1 | 12/2006 | Levy et al. |
| 2007/0077283 A1 | 4/2007 | Quay et al. |
| 2007/0086972 A1 | 4/2007 | Birnbaum |
| 2007/0087957 A1* | 4/2007 | Kidron ................ A61K 9/2013 514/5.9 |
| 2011/0014247 A1 | 1/2011 | Kidron |
| 2011/0046053 A1 | 2/2011 | Kidron |
| 2013/0195939 A1 | 8/2013 | Kidron |
| 2014/0377344 A1 | 12/2014 | Hershko et al. |
| 2015/0335715 A1 | 11/2015 | Kidron et al. |
| 2016/0206703 A1 | 7/2016 | Kidron |

FOREIGN PATENT DOCUMENTS

| | | |
|---|---|---|
| CA | 1223200 A1 | 6/1987 |
| CA | 2621577 A1 | 3/2007 |
| CN | 101095942 A | 2/2008 |
| EP | 0351651 A2 | 1/1990 |
| IL | 68769 A | 2/1986 |
| JP | 02-250823 | 10/1990 |
| JP | 09/208485 A | 8/1997 |
| JP | 10-330287 A | 12/1998 |
| JP | 00/050793 A | 2/2000 |
| JP | 2001/240558 A | 9/2001 |
| JP | 2005-525308 | 8/2005 |

(Continued)

OTHER PUBLICATIONS

Heine et al ('Exenatide versus insulin glargine in patients with sub-optimally controlled type 2 diabetes' Annals of Internal Medicine Oct. 18, 2005 v143(8) pp. 559-569;).*

(Continued)

*Primary Examiner* — Snigdha Maewall
(74) *Attorney, Agent, or Firm* — Sterne, Kessler, Goldstein & Fox P.L.L.C.

(57) ABSTRACT

Described herein are methods and compositions for treating diabetes mellitus, concerning oral pharmaceutical compositions comprising insulin in combination with a GLP-1 analog.

23 Claims, 5 Drawing Sheets
Specification includes a Sequence Listing.

(56) References Cited

FOREIGN PATENT DOCUMENTS

| | | |
|---|---|---|
| JP | 2011-515458 | 8/2011 |
| KR | 01/0069433 | 7/2001 |
| KR | 2001/0069322 | 7/2001 |
| RU | 2104715 | 2/1998 |
| WO | WO 91/14454 | 10/1991 |
| WO | WO 97/03688 | 2/1997 |
| WO | WO 00/24424 | 7/2000 |
| WO | WO 03/057170 A2 | 7/2003 |
| WO | WO 2007/029238 | 3/2007 |
| WO | WO 09/118722 | 10/2009 |
| WO | WO 09/136392 | 11/2009 |

OTHER PUBLICATIONS

International Search Report and Written Opinion for PCT/IL2013/050007 dated Apr. 23, 2013.

International Preliminary Report on Patentability for PCT/IL2013/050007 dated Jul. 17, 2014.

Cure Talk (retrieved from http://trialx.com/curetalk/2012/05/type-2-diabetes-difficult-to-treat-in-children-new-study/ on Apr. 22, 2015, 2 pages).

Joslin Diabetes Center (retrieved from http://www.joslin.org/info/will_diabetes_go_away.html on Apr. 22, 2015, 2 pages).

The Observer (retrieved from http://observer.com/2014/02/tough-to-swallow-paper-trail-breakthrough-leads-to-penny-stock-profiteers/ on Apr. 22, 2015, 5 pages).

WebMD (retrieved from http://www.webmd.com/diabetes/is-there-cure on Apr. 22, 2015, 3 pages).

Agarwal, et al.; "Oral Delivery of Proteins: Effect of Chicken and Duck Ovomucoid on the Stability of Insulin in the Presence of α-Chymotrypsin and Trypsin"; Pharm. Pharmacol. Commun.; (2000); 6: 223-227.

Birk, Trypsin and chymotrypsin inhibitors from soybeans.Methods Enzymol. 1976;45:700-7.

Bar-On, H., et al.; "Enteral Administration of Inslin in the Rat"; Br. J. Pharmac. (1981); 73: 21-24.

Bendayan, et al.; "Biochemical and morpho-cytochemical evidence for the intestinal absorption of insulin in control and diabetic rats. Comparison between the effectiveness of duodenal and colon mucosa"; Diabetologia (1994); 37: 119-126.

Bendayan, et al.; "Morpho-cytochemical and biochemical evidence for insulin absorption by the rat ileal epithelium"; Diabetologia (1990); 33: 197-204.

Carino, et al.; "Oral insulin delivery"; Advanced Drug Delivery Review (1999); 35: 249-257.

Cernea, et al.; "Comparison of pharmacokinetic and pharmacodynamic properties of single-dose oral insulin spray and subcutaneous insulin injection in healthy subjects using the euglycemic clamp technique"; Clinical Therapeutics (2004); 26(12): 2084-2091.

Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (2005); 27(10): 1562-1570.

Cernea, et al.; "Dose-Response Relationship of Oral Insulin Spray in Healthy Subjects"; Diabetes Care (2005); 28(6): 1353-1357.

Chiquette et al., Treatment with exenatide once weekly or twice daily for 30 weeks is associated with changes in several cardiovascular risk markers. Vasc Health Risk Manag. 2012;8:621-9. doi: 10.2147/VHRM.S37969. Epub Nov. 12, 2012.

Cole, et al.; "Challenges and opportunities in the encapsulation of liquid and semi-solid formulations into capsules for oral administration"; Advanced Drug Delivery Reviews (2008); 60: 747-756.

Cournarie, et al.; "Insulin-loaded W/O/W multiple emulsions: comparison of the performances of systems prepared with medium-chain-triglycerides and fish oil"; Euro. J. of Pharmaceutics and BioPharmaceutics; (2004); 58(3): 477-482.

Eldor et al., A Single-Blind, Two-Period Study to Assess the Safety and Pharmacodynarnics of an Orally Delivered GLP-1 Analog (Exenatide) in Healthy SubjectsAmerican Diabetes Association 70th Annual Scientific Sessions, Jun. 25-29, 2010A, Orlando, Florida.

Eldor et al., Open-label study to assess the safety and pharmacodynamics of five oral insulin formulations in healthy subjects.Diabetes Obes Metab. Mar. 2010;12(3):219-23. doi: 10.1111/j.1463-1326.2009.01153.x.

Eldor et al., Novel glucagon-like peptide-1 analog delivered orally reduces postprandial glucose excursions in porcine and canine models. J Diabetes Sci Technol. Nov. 1, 2010;4(6):1516-23.

Gershanik et al., Selfdispersing lipid formulations for improving oral absorption of lipophilic drugs. European Journal of Pharmaceuticals and Biopharmaceutics. 2000;50:179-188.

Gowthamarajan & Kulkarni; Oral Insulin—Fact or Fiction—Possibilities of Achieving Oral Delivery for Insulin; Resonance (2003); 38-46.

Griffin,Calculation of HLB Values of Non-Ionic Surfactants. J Soc Cosmetic Chemists 5:259 (1954).

Hays, et al.; "Prevention and Treatment of Type 2 Diabetes: Current Role of Lifestyle, Natural Product, and Pharmacological Interventions"; Pharmacol. Ther. (2008); 118(2): 181-191.

Heine, et al.; "Exenatide versus Insulin Glargine in Patients with Suboptimally Controlled Type 2 Diabetes"; American College of Physicians—Annals of Internal Medicine 2005; 143(8): 559-569.

Iyer, et al.; "Oral insulin—a review of current status"; Diabetes, Obesity and Metabolism (2010); 12: 179-185.

Kidron, et al.; "A novel per-oral insulin formulation: proof of concept study in non-diabetic subjects"; Diabetic Medicine (2004); 21: 354-357.

Kidron, et al.; "Extended exposure to an oral insulin formulation yields decreased insulin secretion in Type II diabetes subjects"; Diabetes Technology Meeting Nov. 11-13, 2010.

Koide et al., The amino acid sequence of soybean trypsin inhibitor. J. Biochem. 1972;71:165-7.

Lasserson, et al.; "Optimal insulin regimens in type 2 diabetes mellitus: systematic review and meta-analyses"; Diabetologia (2009); 52: 1990-2000.

Li and Deng; "Oil-based formulation for oral delivery of insulin"; J. Pharmacy Pharmacol 2004; 56: 1101-1107.

Ma, et al.; "In Vitro and in Vivo evaluation of a novel oral insulin formulation"; Acta Pharmacologica Sinica (2006); 27(10): 1382-1388.

Mack, et al. "Antiobestiy action of peripheral exenatide (exendin-4) in rodents: effects on food intake, body weight, metabolic status and side-effect measures"; International Journal of Obesity (2006); 30: 1332-1340.

Maher, S. et al.; "Safety and efficacy of sodium caprate in promoting oral drug absorption: from in vitro to the clinic"; Advanced Drug Delivery Reviews; (2009); 61: 1427-1449.

Martinez-Colubi et al., Switching to darunavir/ritonavir monotherapy (DRV/r mx): effect on kidney function and lipid profile. J Int AIDS Soc. Nov. 11, 2012;15(6):18348. doi:10.7448/IAS.15.6.18348

Miyagawa, Jun-ichiro; Med Sci Digest 2008 34(4):147-150.

Miyashita et al., Hepatoprotective effect of tamoxifen on steatosis and non-alcoholic steatohepatitis in mouse models. J Toxicol Sci. 2012;37(5):931-42.

Morishita, et al.; "Hypoglycemic effect of novel oral microspheres of insulin with protease inhibitor in normal and diabetic rats"; Int. J. of Pharma; (1992); 78: 9-16.

Nissan, et al.; "Intestinal absorption of low molecular weight heparin in animals and human subjects"; Haemostasis (2000); 30: 225-232.

Onuki, et al.; "In vivo effects of highly purified docosahexaenoic acid on rectal insulin absorption"; Int. J. of Pharmaceutics; (2000); 198(2): 147-156.

Ozawa et al., The reactive site of trypsin inhibitors.J Biol Chem. Sep. 10, 1966;241(17):3955-61.

Ray Dirks Research; "Novo Nordisk Sitting on $2 Billion in Cash May Look to Acquire Oramed or ISIS for Oral Insulin"; May 31, 2012.

Raz, et al.; "Rectal Administration of Insulin"; Israel Journal of Medical Sciences (1984); 20: 173-175.

(56) References Cited

OTHER PUBLICATIONS

Ryan et al., Assessment of the severity of hypoglycemia and glycemic lability in type 1 diabetic subjects undergoing islet transplantation. Diabetes. Apr. 2004;53(4):955-62.

Sherman, "Oramed Enrolls First Patient in its Phase 2a U.S. Oral Insulin Clinical Trial"; Jul. 8, 2013.

Siepmann et al., Blends of aqueous polymer dispersions used for pellet coating: importance of the particle size. J Control Release. Jul. 20, 2005;105(3):226-39.

Silva-Cunha et al.; "W/O/W multiple emulsions of insulin containing a protease inhibitor and an absorption enhancer: preparation, characterization and determination of stability towards proteases in vitro"; Int. J. of Pharmaceutics; (1997); 158(1): 79-89.

Sprecher et al., Molecular cloning, expression, and partial characterization of two novel members of the ovalbumin family of serine proteinase inhibitors. J Biol Chem. Dec. 15, 1995;270(50):29854-61.

Sun et al., Gene structure, chromosomal localization, and expression of the murine homologue of human proteinase inhibitor 6 (PI-6) suggests divergence of Pi-6 from the ovalbumin serpins. J Biol Chem. Jul. 7, 1995;270(27):16089-96.

Tesauro et al., Effects of GLP-1 on forearm vasodilator function and glucose disposal during hyperinsulinemia in the metabolic syndrome. Diabetes Care. Mar. 2013;36(3):683-9. doi: 10.2337/dc12-0763. Epub Oct. 15, 2012.

Umezawa, Structures and activities of protease inhibitors of microbial origin.Methods Enzymol. 1976;45:678-95.

Yeboah et al., A rapid purification method for soybean Bowman-Birk protease inhibitor using hydrophobic interaction chromatography. Protein Expression and Purification. 1996;7:309-14.

Ziv, et al.; "Absorption of Protein via the Intestinal Wall A Quantitative Model"; Biochemical Pharmacology (1987); 36(7): 1035-1039.

Ziv, et al.; "Bile Salts Promote the Absorption of Insulin from the Rat Colon"; Life Sciences (1981); 29: 803-809.

Ziv, et al.; "Oral administration of insulin in solid form to nondiabetic and diabetic dogs"; Journal of Pharmaceutical Sciences (1994); 83(6): 792-794.

U.S. Appl. No. 12/934,754, filed Sep. 27, 2010, Kidron.
U.S. Appl. No. 14/996,800, filed Jan. 15, 2016, Kidron.
U.S. Appl. No. 13/855,346, filed Apr. 2, 2013, Kidron.
U.S. Appl. No. 14/376,292, filed Aug. 1, 2014, Hershko.
U.S. Appl. No. 14/759,060, filed Jul. 2, 2015, Kidron.
PCT/IL2013/050007, Apr. 23, 2013, International Search Report and Written Opinion.
PCT/IL2013/050007, Jul. 17, 2014 International Preliminary Report on Patentability.

[No Author Listed] Worthington Biochemical Corporation (2016; Trypsin inhibitors C.A.S.: 903581-1. On the web at worthington-biochem.com/TI/default.html.

Koide et al., Studies on soybean trypsin inhibitors. 3. Amino-acid sequences of the carboxyl-terminal region and the complete amino-acid sequence of soybean trypsin inhibitor (Kunitz).Eur J Biochem. Feb. 1, 1973;32(3):417-31.

Morishita et al. Novel oral microspheres of insulin with protease inhibitor protecting from enzymatic degradation. International Journal of Pharmaceutics. 78 (1992) 1-7.

Nadeau et al., Treatment of non-alcoholic fatty liver disease with metformin versus lifestyle intervention in insulin-resistant adolescents. Pediatr Diabetes. Feb. 2009;10(1):5-13. doi: 10.1111/j.1399-5448.2008.00450.x. Epub Aug. 20, 2008.

Park et al., Oral protein delivery: Current status and future prospect. Reactive and Functional Polymers. 71 (2011) 280-287.

Shyangdan et al., Insulin sensitisers in the treatment of non-alcoholic fatty liver disease: a systematic review. Health Technol Assess. Nov. 2011;15(38):1-110. doi: 10.3310/hta15380.

* cited by examiner

| trial sequence | trial no. | Lecithin | GMS | Tween 80 | Gelucire 44/14 | density | foam buildup | test of the suspension in water | sedimentation | decision feasibility | Effectiveness (1=lowest) |
|---|---|---|---|---|---|---|---|---|---|---|---|
| I Lecithin | a | 5% | | | | | 3 | 1-2 | strong, after 2 hours | aborted 18 hours after preparation due to the sedimentation | |
| | b* | 5% | 2% | | | 1.0658 | 2 | 2 | not visible | sent for testing | t.b.d. |
| | c | 10% | | | | | 4 | n.a. | n.a. | aborted due to foam building | |
| II Tween 80 | a | | | 2% | | | 1 | n.a. | strong, after 1 hour | aborted 2 hours after preparation due to the sedimentation | |
| | b | | | 4% | | | 1 | n.a. | strong, after 1 hour | aborted 2 hours after preparation due to the sedimentation | |
| | c | | | 20% | | | 1 | n.a. | strong, after 1 hour | aborted 2 hours after preparation due to the sedimentation | |
| | d | | | 10% | | | 1 | n.a. | strong, after 1 hour | aborted 2 hours after preparation due to the sedimentation | |
| | e | | 2% | 2% | | | 1 | 2-3 | moderate, after 1 hour | aborted 18 hours after preparation due to the sedimentation | |
| | f | | 2% | 4% | | | 1 | 2-3 | moderate, after 1 hour | aborted 18 hours after preparation due to the sedimentation | |
| | g | | 2% | 20% | | | 1 | n.a. | strong, after 1 hour | aborted 2 hours after preparation due to the sedimentation | |
| | h | | 2% | 10% | | | 1 | 3 | moderate, after 1 hour | aborted 18 hours after preparation due to the sedimentation | |

Figure 1

| | | | | | | | | | |
|---|---|---|---|---|---|---|---|---|---|
| III Gelucire 44/14 | a | | | | 2% | | | n.a. | aborted immediately after preparation due to low viscosity |
| | b | | | | 4% | | 1 | stable after 18 hours | aborted after 18 hours due to lower viscosity than IIIj |
| | c | | | | 8% | | 1 | stable after 18 hours | aborted after 18 hours due to lower viscosity than IIIj |
| | d* | 3 | | | 12% | 1.0443 | 1 | a very thin oil layer (1mm)visible after 18 hours | sent for testing | 2 |
| | e* | 6 | | | 12% | 1.0565 | 1 | a very thin oil layer (1mm)visible after 18 hours | sent for testing |
| | g* | | 5 | | 12% | 1.0604 | 1 | a very thin oil layer (1mm)visible after 18 hours | sent for testing | 4 |
| | h* | | 10 | | 12% | 1.0599 | 1 | a very thin oil layer (1mm)visible after 18 hours | sent for testing | 4 |
| | j* | | | | 12% | 1.0644 | 1 | stable after 18 hours | sent for testing | 2 |

Continuation of Figure 1

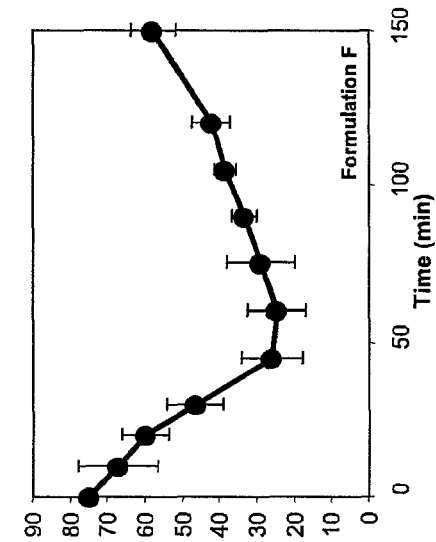
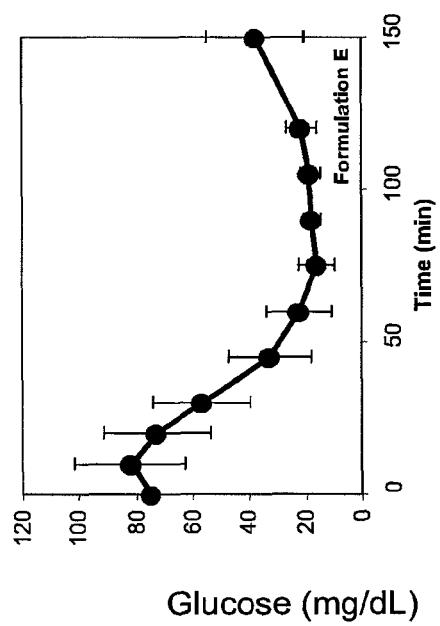
Figure 2B

METHODS AND COMPOSITIONS FOR TREATING DIABETES

RELATED APPLICATIONS

This application is a 35 U.S.C. § 371 National Phase Application of International Application No. PCT/IL2013/050007, filed Jan. 3, 2013, and entitled "METHODS AND COMPOSITIONS FOR TREATING DIABETES," which claims the benefit of U.S. Provisional Patent Application No. 61/631,339, filed Jan. 3, 2012; U.S. Provisional Patent Application No. 61/631,339 is incorporated herein by reference in its entirety.

FIELD

Described herein are methods and compositions for treating diabetes mellitus.

BACKGROUND

Diabetes, specifically the Type II (NIDDM) variety, has emerged in the twenty-first century as an epidemic of global proportions. Numerous long-term complications, including those affecting the kidneys, legs, feet, eyes, heart, nerves, and blood circulation, may result from uncontrolled diabetes. Prevention of these conditions requires comprehensive treatment, requiring life style modification and medication. A number of effective anti-diabetic drugs are available and are generally safe and well tolerated. All the medications become less effective as the disease progresses, and most patients eventually require insulin. Most of the medications are associated with risks of hypoglycemia and weight gain, yet do not alter the inexorable progression of diabetes.

Orally-delivered formulations for protein-based drugs such as insulin are being developed by the present inventor (Ziv et al 1994; Nissan et al 2000, Kidron et al 2004, Eldor et al 2010B, Eldor et al 2010C). One such oral insulin product is scheduled to be tested in Phase II trials and is currently being reviewed for IND status.

The incretin hormone Glucagon-like Peptide 1 (GLP-1), secreted within minutes of food ingestion, is associated with induction of insulin release. Therapies based on GLP-1 are treatment options for Type 2 Diabetes Mellitus (T2DM) that act through a variety of complementary mechanisms. The most intriguing aspect of the incretins is the fact that they cause insulin release in a glucose-dependent manner and are thought to have a low risk of inducing hypoglycemia. Furthermore, the incretins seem to be weight-neutral (or weight-reducing), preserve beta-cell mass, and possibly also induce neogenesis of insulin-secreting cells.

However, clinical use of the native GLP-1 is limited due to its rapid enzymatic inactivation, resulting in a half-life of 2-3 minutes. To overcome this obstacle, long-acting degradation-resistant peptides, both natural and synthetic, referred to as GLP-1 mimetic agents or analogues, have been designed and tested.

To date, GLP-1 analogues are only available as injectable dosage forms. The present inventor is developing an oral exenatide GLP-1 analogue capsule. A first-in-humans trial (n=4) testing its safety in healthy humans demonstrated retained biological functionality of orally delivered exenatide (Eldor et al 2010A).

SUMMARY

To the inventor's knowledge, oral insulin formulations have not been tested in combination with oral GLP-1 analogue formulations. The data provided herein illustrate a previously-unrecognized, strong cooperative interaction between these components when formulated as described herein. This enables a potent anti-diabetes effect in a convenient form that both facilitates patent compliance and also mimics physiological first-pass metabolism of insulin and GLP-1. These results provide a route to an entirely new class of therapeutic modalities.

The terms "protein" and "peptide" are used interchangeably herein. Neither term is intended to confer a limitation of the number of amino acids present, except where a limitation is explicitly indicated.

BRIEF DESCRIPTION OF THE DRAWINGS

The following figures are by way of illustrative example and are not meant to be taken as limiting the claimed invention.

FIG. 1. Testing of various emulsifier formulations. Foam buildup score was from 1-5, where 1 indicates no foam, and 5 indicates no liquid visible because of the foam. For the suspension test, the numbers 1-5 indicate full phase separation; partial phase separation with some larger oil bubbles; small oil bubble, milky consistency; no bubbles initially, with later phase separation; and stable emulsion, respectively.

FIGS. 2A and 2B. Blood glucose profiles following administration of oral insulin formulations containing various emulsifiers. 2A: Formulations A (upper left), B (lower left), C (upper right), and D (lower right). 2B: Formulations E (left) and F (right).

DETAILED DESCRIPTION OF THE EMBODIMENTS

Figure 2A:
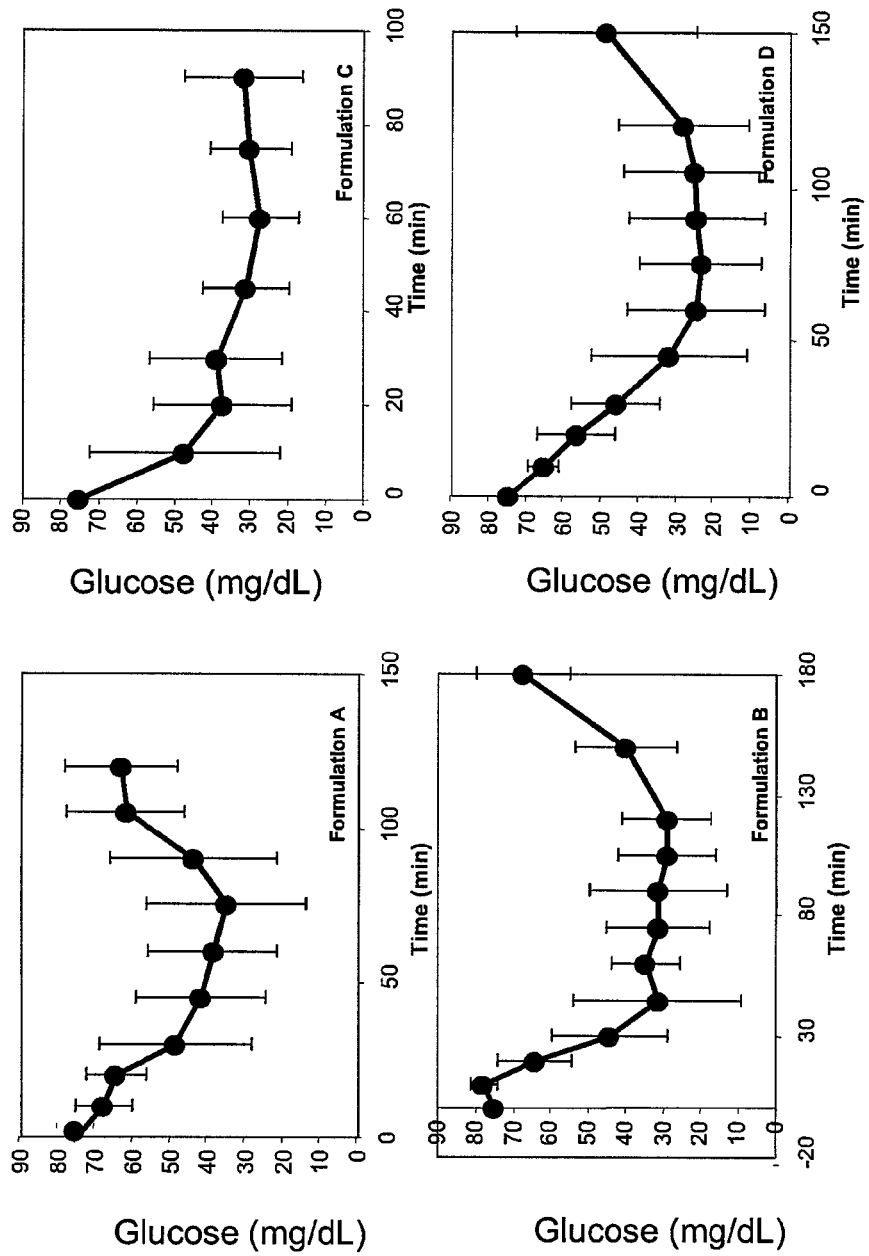

Provided herein is a pharmaceutical composition for oral delivery, comprising an oil-based liquid formulation, the oil-based liquid formulation comprising an insulin, a GLP-1 analogue, a trypsin inhibitor, and a chelator of divalent cations, wherein the oil-based liquid formulation is surrounded by a coating or capsule that resists degradation in the stomach.

Another embodiment provides a multi-component oral pharmaceutical composition, comprising: (a) a first oil-based liquid formulation, the first oil-based liquid formulation comprising an insulin, a trypsin inhibitor, and a chelator of divalent cations; and (b) a second oil-based liquid formulation, the second oil-based liquid formulation comprising a GLP-1 analogue, a trypsin inhibitor, and a chelator of divalent cations; wherein each of the first oil-based liquid formulation and the second oil-based liquid formulation is surrounded by a coating or capsule that resists degradation in the stomach. In some embodiments, the two liquid formulations can be in separate dosage forms. In other embodiments, the two liquid formulations are in the same dosage form; for example, in separate encased compartments within the same pill.

"Liquid" as used herein refers to a phase that flows freely and has a constant volume under ambient conditions. Fish oil, for instance, is a liquid under ambient conditions. The term includes oil-based solutions, suspensions, and combinations thereof. In alternative embodiments, the term may refers to a composition that has a viscosity within the range of 1-1000 millipascal seconds, inclusive, at 20° C.

In certain embodiments, the different components of a multi-component pharmaceutical composition are indicated for co-administration together. "Co-administration", in this regard, may refer either to simultaneous administration or, in another embodiment, to administration within 30 minutes of each other. In still other embodiments, the different components are indicated for administration in a particular order, separated by a set time interval that will typically be 30 minutes or less. For example, the insulin-containing dosage form may be indicated for administration 2-10 minutes after the exenatide-containing dosage form; in other embodiments, 10-20 minutes after the exenatide-containing dosage form; in other embodiments, 20-30 minutes after the exenatide-containing dosage form; and in other embodiments, 30-60 minutes after the exenatide-containing dosage form. Oral dosage forms such as those provided herein lend themselves to sequential administration more than injected dosage forms, since regimens requiring repeated injections are likely to be associated with low rates of compliance.

According to other aspects, a combination medicament for treatment of type 2 diabetes is provided, said combination medicament comprising
  insulin, at least one trypsin inhibitor, and a chelator of divalent cations, and
  a GLP-1 analogue from the group consisting of exenatide, liraglutide, AC3174, taspoglutide, lixisenatide, semaglutide, albiglutide, exendin-9, LY2189265, and CJC-1134-PC,
  all comprised jointly in an oil-based liquid formulation in a dosage form for oral delivery.

Insulin Proteins and GLP-1 Analogues

Insulin proteins and GLP-1 analogues for use as described herein are in some embodiments isolated prior to their introduction into the described pharmaceutical compositions. "Isolated" in this regard excludes provision of the insulin and/or GLP-1 analogue as a homogenized tissue preparation or other form containing substantial amounts of contaminating proteins. An example of an isolated protein or peptide is a recombinant protein or peptide. An alternative embodiment is a synthetic protein or peptide.

A person skilled in the art will appreciate in light of the present disclosure that various types of insulin are suitable for the described methods and compositions. Exemplary insulin proteins include but are not limited to both wild-type and mutated insulin proteins, including synthetic human insulin, synthetic bovine insulin, synthetic porcine insulin, synthetic whale insulin, and metal complexes of insulin, such as zinc complexes of insulin, protamine zinc insulin, and globin zinc.

Various classes of insulin may also be utilized, for example fast-acting insulin, lente insulin, semilente insulin, ultralente insulin, NPH insulin, glargine insulin, lispro insulin, aspart insulin, or combinations of two or more of the above types of insulin.

In certain embodiments, the insulin of the described methods and compositions is wild-type human insulin (Uniprot ID P01308). In some embodiments, human insulin is produced as a recombinant protein in bacterial cells. In other embodiments, human insulin is produced synthetically.

GLP-1 analogues are also referred to in the art as GLP-1 mimetics. A person of skill in the art will appreciate that the described compositions may include at least one of the following GLP-1 analogues: exenatide (Byetta™; CAS no. 141732-76-5; SEQ ID NO: 4), lixisenatide (CAS no. 320367-13-3), liraglutide (CAS no. 204656-20-2), exendin-9 (CAS no. 133514-43-9), AC3174 ([Leu(14)]exendin-4, Amylin Pharmaceuticals, Inc.), taspoglutide (CAS no. 275371-94-3), albiglutide (CAS no. 782500-75-8), semaglutide (CAS no. 910463-68-2), LY2189265 (Dulaglutide™; CAS no. 923950-08-7), and CJC-1134-PC (a modified Exendin-4 analogue conjugated to recombinant human albumin manufactured by ConjuChem™). All CAS records were accessed on Dec. 19, 2011. Thus, in certain embodiments, the described method or composition utilizes any of the above-listed GLP-1 analogues. In other embodiments, one of the above-listed GLP-1 analogues is selected. Those of skill in the art will appreciate in light of the findings of described herein that other GLP-1 analogues can also be utilized.

Therapeutic insulin and GLP-1 proteins suitable for use in the present invention include derivatives that are modified (i.e., by the covalent attachment of a non-amino acid residue to the protein). For example, but not by way of limitation, the protein includes proteins that have been modified, e.g., by glycosylation, acetylation, PEGylation, phosphorylation, amidation, or derivatization by known protecting/blocking groups. High-MW PEG can be attached to therapeutic proteins with or without a multifunctional linker either through site-specific conjugation of the PEG to the N- or C-terminus thereof or via epsilon-amino groups present on lysine residues. Additionally, the derivative may contain one or more non-classical amino acids, for example D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, and Nα-methyl amino acids.

Emulsifiers

In certain embodiments, an oil-based liquid formulation utilized in the described methods and pharmaceutical compositions, or in other embodiments, each of the oil-based liquid formulation that is present, further comprises a component provided as a mixture of (a) a monoacylglycerol (monoglyceride), a diacylglycerol (diglyceride), a triacylglycerol (triglyceride), or a mixture thereof; and (b) a polyethylene glycol (PEG) ester of a fatty acid. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. In certain preferred embodiments, monoacylglycerols, diacylglycerols, or triacylglycerols utilized in the described methods and compositions, for example those used to general PEG esters, are from an oil source that is Generally Recognized As Safe (GRAS).

Examples of GRAS oil sources are coconut oil, corn oil, peanut oil, soybean oil, Myvacet 9-45 (Diacetylated monoglycerides of C-18 fatty acids).

A more specific embodiment of (a) is a mixture of $C_8$-$C_{18}$ monoacylglycerols, diacylglycerols, and triacylglycerols. A more specific embodiment of component (b) is a mixture of PEG monoesters and diesters of a mixture of $C_8$-$C_{18}$ fatty acids.

In other, more specific embodiments, the liquid formulation further comprises a free PEG.

In alternate embodiments, an oil-based liquid formulation utilized in the described methods and pharmaceutical compositions, or in other embodiments, each of the oil-based liquid formulation that is present, further comprises a PEG ester of a monoacylglycerol, a diacylglycerol, a triacylglycerol, or a mixture thereof. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. In more specific embodiments, an additional non-ionic detergent, for example a polysorbate-based detergent, is present in addition to the PEG ester. In other, more specific embodiments, a free PEG is also present. In still more specific embodiments, both an additional non-ionic detergent and a free PEG are also present.

In a still more specific embodiment of the described methods and compositions, a liquid formulation used therein comprises: (a) a mixture of $C_8$-$C_{18}$ monoacylglycerols, diacylglycerols, and triacylglycerols; (b) PEG-32 monoesters and diesters of a mixture of $C_8$-$C_{18}$ fatty acids; and (c) free PEG-32. Even more specifically, the weight/weight ratio of component (a) to components (b)+(c) is between 10:90-30:70 inclusive; more specifically between 15:85-25:75 inclusive; more specifically 20:80. In certain embodiments, components (a)-(c) together constitute 8-16% weight/weight inclusive of the oil-based liquid formulation. In more specific embodiments, the amount is 9-15% inclusive. In more specific embodiments, the amount is 10-14% inclusive. In more specific embodiments, the amount is 11-13% inclusive. In more specific embodiments, the amount is 12%.

In other embodiments, an oil-based liquid formulation utilized in the described methods and pharmaceutical compositions further comprises a self-emulsifying component, which may or may not be one of the mixtures of components described in the preceding paragraphs. "Self-emulsifying component" in some embodiments refers to a component that spontaneously forms an emulsion. Typically, such components will form an emulsion under on contact with aqueous media, forming a fine dispersion i.e. a microemulsion (SMEDDS). Certain embodiments of such components comprise a mixture of triacylglycerols and a high hydrophile/lipophile balance (HLB; see Griffin W C: "Calculation of HLB Values of Non-Ionic Surfactants," J Soc Cosmetic Chemists 5:259 (1954)) surfactant. Other embodiments of the self-emulsifying component have a waxy, semi-solid consistency.

Preferably, the HLB of a self-emulsifying component utilized in the described methods and compositions is 10 or greater. In other embodiments, it is between 11-19 inclusive. In other embodiments, it is between 12-18 inclusive. In other embodiments, it is between 12-17 inclusive. In other embodiments, it is between 12-16 inclusive, which is indicative of an oil-in-water (O/W) emulsifier. In other embodiments, it is between 13-15 inclusive. In other embodiments, it is 14. Still more specific embodiments of self-emulsifying components have an HLB of 12-16 inclusive and comprise medium and long chain triacylglycerols conjugated to PEG, free triacylglycerols, and free PEG. In other embodiments, the self-emulsifying component has an HLB of 12-16 inclusive and consists of a mixture of medium and long chain triacylglycerols conjugated to PEG, free triacylglycerols, and free PEG. In other embodiments, the self-emulsifying component has an HLB of 14 and comprises medium and long chain triacylglycerols conjugated to PEG, free triacylglycerols, and free PEG. In other embodiments, the self-emulsifying component has an HLB of 14 and consists of a mixture of medium and long chain triacylglycerols conjugated to PEG, free triacylglycerols, and free PEG.

Certain, more specific embodiments utilize self-emulsifying components that comprise (a) a monoacylglycerol, a diacylglycerol, a triacylglycerol, or a mixture thereof; and (b) a polyethylene glycol (PEG) ester of a fatty acid. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. A more specific embodiment is a mixture of $C_8$-$C_{18}$ monoacylglycerols, diacylglycerols, and triacylglycerols.

A more specific embodiment of component (b) is a mixture of PEG monoesters and diesters of a mixture of $C_8$-$C_{18}$ fatty acids.

In other, more specific embodiments, the self-emulsifying component further comprises molecules of free PEG.

Preferred lengths of PEG moieties for use in the described compositions and methods contain between 5-100 monomers. In more specific embodiments, the PEG may contain between 15-50 monomers. In still more specific embodiments, the PEG may contain between 25-40 monomers. In more specific embodiments, the PEG may contain 32 monomers.

In a still more specific embodiment of the described methods and compositions, a self-emulsifying component used therein comprises: (a) a mixture of $C_8$-$C_{18}$ monoacylglycerols, diacylglycerols, and triacylglycerols; (b) PEG-32 monoesters and diesters of a mixture of $C_8$-$C_{18}$ fatty acids; and (c) free PEG-32; and the weight/weight ratio of component (a) to components (b)+(c) is 20:80. In certain embodiments, such a component constitutes 8-16% weight/weight inclusive of the oil-based liquid formulation. In more specific embodiments, the amount is 9-15% inclusive. In more specific embodiments, the amount is 10-14% inclusive. In more specific embodiments, the amount is 11-13% inclusive. In more specific embodiments, the amount is 12%.

Examples of self-emulsifying components meeting the above specifications are Gelucire™ 44/14, Gelucire™ 53/10, and Gelucire™ 50/13. A particularly preferred example is Gelucire™ 44/14. The suffixes 44 and 14 refer respectively to its melting point and its hydrophilic/lypophilic balance (HLB). Gelucire™ 44/14 (Gattefossé SAS, Saint-Priest, France) is obtained by polyglycolysis of hydrogenated coconut oil (medium and long chain triacylglycerols with PEG-32. It has a hydrophile/lipophile balance of 14. It is composed of a defined admixture of $C_8$-$C_{18}$ mono-, di- and triacylglycerols (20% w/w); PEG-32 mono- and diesters and free PEG-32 (80% w/w). The main fatty acid present is lauric acid, accounting for 45% on average of the total fatty acid content. It is a solid dispersion composed of a PEG ester fraction under a lamellar phase of 120 Å with a helical conformation and an acylglycerol fraction under a hexagonal packing. The main products of simulated gastrointestinal lipolysis of Gelucire™ 44/14 are PEG-32 mono and diesters.

Non-Ionic Detergents

In certain embodiments, the oil-based liquid formulation utilized in the described methods and pharmaceutical compositions further comprises a non-ionic detergent in addition to the self-emulsifying component. In certain embodiments, the non-ionic detergent is selected from the group consisting of polysorbate-20, polysorbate-40, polysorbate-80, lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose, carboxymethyl cellulose, n-octylglucoside, n-dodecylglucoside, n-dodecylmaltoside, octanoyl-N-methylglucamide, decanoyl-N-methylglucamide, Triton™-X-100, Triton™-X-114, Thesit™, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), and N-dodecyl=N,N-dimethyl-3-ammonio-1-propane sulfonate. In other embodiments, one of the above-listed non-ionic detergents is selected.

In certain, more specific embodiments, a non-ionic detergent used in the described methods and compositions is a polysorbate-based detergent. Examples of polysorbate-based detergent are detergents derived by covalently bonding polyethoxylated sorbitan to a fatty acid. More specific embodiments of polysorbate-based detergents are polysorbate-20, polysorbate-40, and polysorbate-80.

For example, polysorbate 80 (Tween-80) is a mild, non-ionic detergent derived from polyethoxylated sorbitan and oleic acid and having the following structure:

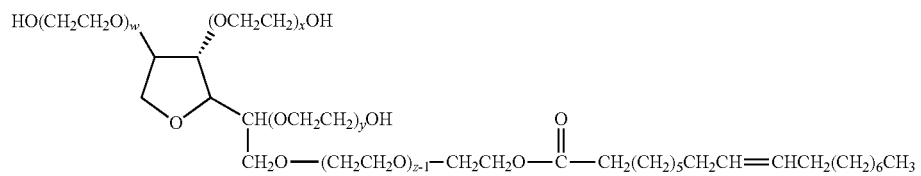

Sum of $w + x + y + z = 20$

In the case of polysorbate 80, the moiety shown on the right side is a mixture of fatty acids, containing 60-70% oleic acid (as depicted), with the balance being primarily linoleic, palmitic, and stearic acids.

In a more specific embodiment, the polysorbate 80 constitutes 3-10% weight/weight inclusive of an oil-based liquid formulation used in the described methods and compositions. In a more specific embodiment, the percentage is 4-8% inclusive. In a more specific embodiment, the percentage is 4.5-6% inclusive. In a more specific embodiment, the percentage is 5%.

Dosages

Alternatively or in addition, the insulin and/or GLP-1 analogue present in the described compositions or used in the described methods is present in a subclinical amount. The term "subclinical amount" in this context refers to an amount less than that required to elicit a complete desired physiological effect, for example control of post-prandial blood glucose levels, in the context of its formulation and the patient. Accordingly, a subclinical dose of insulin would be less than that required using formulations similar to those described herein that contain insulin but lack a GLP-1 analogue; or, in a more specific embodiment, a formulation identical except for the absence of the GLP-1 analogue. Similarly, a subclinical dose of a GLP-1 analogue would be less than that required using formulations similar to those described herein that contain a GLP-1 analogue but lack insulin; or, in a more specific embodiment, a formulation identical except for the absence of the insulin.

Those skilled in the art will appreciate, in light of the present disclosure, that characterization of a dose as subclinical will depend on the weight and health status (including insulin resistance, if relevant) of the patient, the circumstances of the administration, co-administration of other diabetes medications, the robustness of the active ingredient and the excipients, and the desired physiological effect. For example, studies to date of oral formulations similar to those described herein, but containing insulin only, have shown that 8 mg of an encapsulated oral formulation in combination with a protease inhibitor and EDTA, in fish oil (similar to the one described herein but lacking exenatide) is a subclinical dose for fasting, adult, human Type 2 diabetic patients, if the goal is a robust change in blood glucose levels; while 16 mg. is a clinical dose under the same circumstances. Doses of the same formulation necessary to achieve modulation of post-prandial glucose excursions in the same patients have not been determined, but are likely to be slightly higher. However, doses such as these also depend on the potency of the formulation, and thus the clinical dose threshold may be slightly lower if a more potent protease inhibitor is used, for example. Determination of a subclinical dose for a particular set of circumstances, for example via empirical testing, is well within the ability of one skilled in the art.

In more specific embodiments, the subclinical amount of insulin of the described methods and compositions is between 6-16 mg inclusive for an adult patent having diabetes mellitus, for example Type 2 diabetes mellitus (T2DM), for example for preventing post-prandial glucose excursions when administered between 30-60 minutes (min) before a meal, in more specific embodiments 30 min, 45 min, or 60 min before a meal. In other embodiments, the subclinical amount is between 6-14 mg inclusive. In other embodiments, the subclinical amount is between 6-12 mg inclusive. In other embodiments, the subclinical amount is between 6-10 mg inclusive. In other embodiments, the subclinical amount is 8 mg. In other embodiments, the subclinical amount is 12 mg. In other embodiments, the subclinical amount is between 8-16 mg inclusive. In other embodiments, the subclinical amount is between 8-14 mg inclusive. In other embodiments, the subclinical amount is between 8-12 mg inclusive. In other embodiments, the subclinical amount is between 8-10 mg inclusive. In other embodiments, the subclinical amount is 16 mg. In other embodiments, the subclinical amount is between 10-16 mg inclusive. In other embodiments, the subclinical amount is between 10-14 mg inclusive. In other embodiments, the subclinical amount is between 10-18 mg inclusive.

In other embodiments, the subclinical amount of insulin of the described methods and compositions is between 0.06-0.16 mg/kg (milligrams per kilogram body weight) inclusive for an adult patent having T2DM, for example for preventing post-prandial glucose excursions when administered before a meal. In other embodiments, the subclinical amount is between 0.06-0.14 mg/kg inclusive. In other embodiments, the subclinical amount is between 0.06-0.12 mg/kg inclusive. In other embodiments, the subclinical amount is between 0.06-0.10 mg/kg inclusive. In other embodiments, the subclinical amount is 0.08 mg/kg. In other embodiments, the subclinical amount is 0.12 mg/kg. In other embodiments, the subclinical amount is 0.16 mg/kg. In other embodiments, the subclinical amount is between 0.08-0.16 mg/kg inclusive. In other embodiments, the subclinical amount is between 0.08-0.14 mg/kg inclusive. In other embodiments, the subclinical amount is between 0.08-0.12 mg/kg inclusive. In other embodiments, the subclinical amount is between 0.08-0.10 mg/kg inclusive. In other embodiments, the subclinical amount is between 0.10-0.16 mg/kg inclusive. In other embodiments, the subclinical amount is between 0.10-0.18 mg/kg inclusive. In other embodiments, the subclinical amount is between 0.10-0.14 mg/kg inclusive.

In still other embodiments, the subclinical amount of insulin is an amount corresponding to one of the above amounts or ranges for an adult, adjusted per body weight for a pediatric patient. In other embodiments, the insulin is present in a subclinical amount adjusted for a pediatric patient, and the GLP-1 analogue is also present in a subclinical amount adjusted for a pediatric patient.

The above amounts may be for wild-type human insulin, or in another embodiment, for one of the other types of insulin known in the art.

In other, more specific embodiments, a subclinical amount of a GLP-1 analogue is present in a dosage form of the described methods and compositions. In some embodiments, 150 micrograms (mcg), 200 mcg, 250 mcg, or 300 mcg is considered a subclinical dose for adult, human subjects with T2DM for example for preventing post-prandial glucose excursions when administered between 30-60 min before a meal, in more specific embodiments 30 min, 45 min, or 60 min before a meal. In other embodiments, the subclinical amount of GLP-1 analogue is between 100-400 mcg inclusive for an adult patent having T2DM. In other embodiments, the subclinical amount is between 100-300 mcg. inclusive. In other embodiments, the subclinical amount is between 100-250 mcg. inclusive. In other embodiments, the subclinical amount is between 100-200 mcg. inclusive. In other embodiments, the subclinical amount is between 100-150 mcg. inclusive. In other embodiments, the subclinical amount is 100 mcg. In other embodiments, the subclinical amount is 150 mcg. In other embodiments, the subclinical amount is 200 mcg. In other embodiments, the subclinical amount is 250 mcg. In other embodiments, the subclinical amount is 300 mcg. In other embodiments, the subclinical amount is between 150-400 mcg. In other embodiments, the subclinical amount is between 150-300 mcg. inclusive. In other embodiments, the subclinical amount is between 150-250 mcg. inclusive. In other embodiments, the subclinical amount is between 150-200 mcg. inclusive.

In other embodiments, the subclinical amount of GLP-1 analogue of the described methods and compositions is between 0.100-0.400 mcg/kg inclusive for an adult patent having T2D, for example for preventing post-prandial glucose excursions when administered before a meal. In other embodiments, the subclinical amount is between 0.100-0.300 mcg/kg inclusive. In other embodiments, the subclinical amount is between 0.100-0.250 mcg/kg inclusive. In other embodiments, the subclinical amount is between 0.100-0.200 mcg/kg inclusive. In other embodiments, the subclinical amount is between 0.100-0.150 mcg/kg inclusive. In other embodiments, the subclinical amount is 0.100 mcg/kg. In other embodiments, the subclinical amount is 0.150 mcg/kg. In other embodiments, the subclinical amount is 0.200 mcg/kg. In other embodiments, the subclinical amount is 0.250 mcg/kg. In other embodiments, the subclinical amount is 0.300 mcg/kg. In other embodiments, the subclinical amount is between 0.150-0.400 mcg/kg inclusive. In other embodiments, the subclinical amount is between 0.150-0.300 mcg/kg inclusive. In other embodiments, the subclinical amount is between 0.150-0.250 mcg/kg inclusive. In other embodiments, the subclinical amount is between 0.100-0.200 mcg/kg inclusive.

In other embodiments, the subclinical amount of GLP-1 analogue is an amount corresponding to one of the above amounts or ranges for an adult, adjusted per body weight for a pediatric patient. In other embodiments, the GLP-1 analogue is present in a subclinical amount adjusted for a pediatric patient, and the insulin is also present in a subclinical amount adjusted for a pediatric patient, for example an amount corresponding to 4-12 mg inclusive for an adult patent, adjusted for the weight of the a pediatric patient.

The above amounts may be for exenatide, or in another embodiment, for one of the other GLP-1 analogues known in the art.

In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 8-16 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 8-12 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 12-16 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 16-24 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 24-32 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 12-16 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 8 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 12 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 16 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 20 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 24 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 28 mg insulin inclusive. In other embodiments, the described dosage form contains exenatide in an amount of between 100-600 mcg inclusive, 100-500 mcg inclusive, 100-400 mcg inclusive, 100-300 mcg inclusive, 200-600 mcg inclusive, 200-500 mcg inclusive, 200-400 mcg inclusive, 200-300 mcg inclusive, 150-300 mcg inclusive, or 150-250 mcg inclusive; together with 32 mg insulin inclusive.

In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 150-300 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 300-450 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 450-600 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 100-150 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 150-200 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 200-250 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 250-300 mcg exenatide inclusive.

In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 100 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 200 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 250 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 300 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 400 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 500 mcg exenatide inclusive. In other embodiments, the described dosage form contains insulin in an amount of 8-32 mg inclusive, 8-28 mg inclusive, 8-24 mg inclusive, 8-20 mg inclusive, 8-16 mg inclusive, 8-12 mg inclusive, 12-32 mg inclusive, 16-32 mg inclusive, 20-32 mg inclusive, 24-32 mg inclusive, 12-24 mg inclusive, 16-24 mg inclusive, 12-20 mg inclusive, or 16-20 mg inclusive; together with 600 mcg exenatide inclusive.

In other embodiments, the described dosage form contains 8-16 mg insulin inclusive and 150-300 mcg. exenatide. In other embodiments, the described dosage form contains 8-12 mg insulin inclusive and 150-300 mcg. exenatide. In other embodiments, the described dosage form contains 12-16 mg insulin inclusive and 150-300 mcg. exenatide. In other embodiments, the described dosage form contains 6-16 mg insulin inclusive and 150-300 mcg. exenatide.

In other embodiments, the described dosage form contains 8-16 mg insulin inclusive and 100-400 mcg. exenatide. In other embodiments, the described dosage form contains 8-12 mg insulin inclusive and 100-400 mcg. exenatide. In other embodiments, the described dosage form contains 12-16 mg insulin inclusive and 100-400 mcg. exenatide. In other embodiments, the described dosage form contains 6-16 mg insulin inclusive and 100-400 mcg. exenatide.

In other embodiments, the described dosage form contains 8-16 mg insulin inclusive and 100-200 mcg. exenatide. In other embodiments, the described dosage form contains 8-12 mg insulin inclusive and 100-200 mcg. exenatide. In other embodiments, the described dosage form contains 12-16 mg insulin inclusive and 100-200 mcg. exenatide. In other embodiments, the described dosage form contains 6-16 mg insulin inclusive and 100-200 mcg. exenatide.

In other embodiments, the described dosage form contains 8-16 mg insulin inclusive and 200-400 mcg. exenatide. In other embodiments, the described dosage form contains 8-12 mg insulin inclusive and 200-400 mcg. exenatide. In other embodiments, the described dosage form contains 12-16 mg insulin inclusive and 200-400 mcg. exenatide. In other embodiments, the described dosage form contains 6-16 mg insulin inclusive and 200-400 mcg. exenatide.

In other embodiments, the described dosage form contains 8-16 mg insulin inclusive and 150-300 mcg. exenatide.

In some embodiments, the patient receiving the described pharmaceutical composition is receiving a small-molecule DM therapeutic agent such as Metformin and/or a thiazolidinedione (TZD). In other embodiments, the patient is not receiving a small-molecule DM therapeutic agent. The described compositions are believed to be effective in either instance.

Protease Inhibitors

As used herein, the term "trypsin inhibitor" refers to any agent capable of inhibiting the action of trypsin on a substrate. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241:3955; and Y. Birk, 1976, Meth. Enzymol. 45:700.

Some trypsin inhibitors known in the art are specific to trypsin, while others inhibit trypsin and other proteases such as chymotrypsin. Trypsin inhibitors can be derived from animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, or phenylmethanesulfonyl fluoride. As used herein, an arginine or lysine mimic is a compound that is capable of binding to the $P^1$ pocket of trypsin and/or interfering with trypsin active site function.

In certain embodiments, the trypsin inhibitor utilized in methods and compositions of the present invention is selected from the group consisting of lima bean trypsin inhibitor, aprotinin, (a.k.a. pancreatic trypsin inhibitor or basic pancreatic trypsin inhibitor [BPTI]; Uniprot No. P00974 [database accessed on Jan. 2, 2013]), Kazal inhibitor (pancreatic secretory trypsin inhibitor), ovomucoid, Alpha 1-antitrypsin, Cortisol binding globulin, Centerin ([SER-PINA9/GCET1 (germinal centre B-cell-expressed transcript 1)], PI-6 (Sun et al 1995), PI-8 (Sprecher et al 1995), Bomapin, a Glade A serpin [for example Serpina3 (NCBI Gene ID: 12; database accessed on Dec. 27, 2012), Serpina6 (NCBI Gene ID: 866; database accessed on Dec. 27, 2012), Serpina12 (NCBI Gene ID: 145264; database accessed on Dec. 27, 2012); Serpina10 (NCBI Gene ID: 51156; database accessed on Dec. 27, 2012); Serpina7 (NCBI Gene ID: 6906; database accessed on Dec. 27, 2012); Serpina9 (NCBI Gene ID: 327657; database accessed on Dec. 27, 2012); Serpina11 (NCBI Gene ID: 256394; database accessed on Dec. 27, 2012); Serpina13 (NCBI Gene ID: 388007; database accessed on Dec. 27, 2012); Serpina2 (NCBI Gene ID: 390502; database accessed on Dec. 27, 2012); and Serpina4 (NCBI Gene ID: 5104; database accessed on Dec. 27, 2012)] Yukopin (SerpinB12; Gene ID: 89777; database accessed on Dec. 27, 2012), antipain, benzamidine, 3,4-dichloroisocoumarin, diisopropylfluorophosphate, and gabexate mesylate. In other embodiments, more than one, for example 2, 3, or 4, of the above inhibitors is selected.

A representative precursor sequence of aprotinin is:

```
                                        (SEQ ID NO: 1)
MKMSRLCLSV ALLVLLGTLA ASTPGCDTSN QAKAQRPDFC

LEPPYTGPCK ARIIRYFYNA KAGLCQTFVY GGCRAKRNNF

KSAEDCMRTC GGAIGPWENL.
```

Of these 100 residues, residues 1-21 are the signal peptide, 22-35 and 94-100 are propeptides, and the mature chain BBI chain is composed of residues 36-93 (58 AA).

In other embodiments, the trypsin inhibitor is derived from soybean. Trypsin inhibitors derived from soybean (*Glycine max*) are readily available and are considered to be safe for human consumption. They include, but are not limited to, SBTI, KTI (Kuntz Trypsin Inhibitor), for example KTI3, and BBI (Bowman-Birk inhibitor; Uniprot number P01055 [database accessed on Jan. 3, 2013]). SBTI is composed of KTI, which inhibits trypsin, and BBI, which inhibits trypsin and chymotrypsin. Such trypsin inhibitors are available for example from Sigma-Aldrich, St. Louis, Mo., USA.

A representative precursor sequence of BBI is:

```
                                     (SEQ ID NO: 2)
MVVLKVCLVL LFLVGGTTSA NLRLSKLGLL MKSDHQHSND

DESSKPCCDQ CACTKSNPPQ CRCSDMRLNS CHSACKSCIC

ALSYPAQCFC VDITDFCYEP CKPSEDDKEN.
```

Of these 110 residues, residues 1-19 are the signal peptide, 20-39 are a propeptide, and the mature chain BBI chain is composed of residues 40-110 (71 AA).

KTI3 has Uniprot number P01070 (database accessed on Jan. 3, 2013). A representative precursor sequence of KTI3 is:

```
                                     SEQ ID NO: 3)
MKSTIFFLFL FCAFTTSYLP SAIADFVLDN EGNPLENGGT

YYILSDITAF GGIRAAPTGN ERCPLTVVQS RNELDKGIGT

IISSPYRIRF IAEGHPLSLK FDSFAVIMLC VGIPTEWSVV

EDLPEGPAVK IGENKDAMDG WFRLERVSDD EFNNYKLVFC

PQQAEDDKCG DIGISIDHDD GTRRLVVSKN KPLVVQFQKL

DKESLAKKNH GLSRSE
```

Of the above sequence, residues 1-24 are the signal peptide, 206-216 are a propeptide, and the mature KTI chain is composed of residues 25-205 (181 AA).

In other embodiments, a method or oral pharmaceutical composition described herein utilizes two trypsin inhibitors. In other embodiments, more than two trypsin inhibitors are present. In other embodiments, three trypsin inhibitors are present. In other embodiments, four trypsin inhibitors are present. In other embodiments, two of the trypsin inhibitors are SBTI and aprotinin. In yet other embodiments, the only two trypsin inhibitors are SBTI and aprotinin. In still other embodiments, the only two trypsin inhibitors are isolated BBI and isolated aprotinin.

In other embodiments, a chymotrypsin inhibitor is present together with a trypsin inhibitor. In other embodiments, when the chymotrypsin inhibitor is also a trypsin inhibitor, another trypsin inhibitor is also present. Non-limiting examples of a trypsin inhibitor and a trypsin/chymotrypsin inhibitor are isolated KTI, which inhibits trypsin, and isolated BBI (Bowman-Birk inhibitor), which inhibits trypsin and chymotrypsin; these are present together in the composition, in some embodiments.

Chelators of Divalent Cations

The chelator of divalent cations utilized in the described methods and compositions is, in one embodiment, any physiologically acceptable compound having a high affinity for at least one of calcium, magnesium, and manganese ions. In another embodiment, the chelator is selected from the group consisting of citrate or a salt thereof; ethylenediamine tetracetic acid (EDTA) or a salt thereof (for example disodium EDTA and calcium disodium EDTA); EGTA (ethylene glycol tetraacetic acid) or a salt thereof; diethylene triamine pentaacetic acid (DTPA) or a salt thereof; and BAPTA (1,2-bis(o-aminophenoxy)ethane-N,N,N',N'-tetraacetic acid) or a salt thereof. In other embodiments, one of the above-listed chelators is utilized. In more specific embodiments, the chelator is EDTA.

Oils

Pharmaceutical compositions and methods described herein utilize one or more oils as the basis of their liquid phase. In certain embodiments, the oil may be any physiologically acceptable oil that is liquid at ambient temperature.

In more specific embodiments, the oil comprises an omega-3 fatty acid. In other embodiments, the omega-3 fatty acid is an omega-3 polyunsaturated fatty acid. In another embodiment, the omega-3 fatty acid is DHA, an omega-3, polyunsaturated, 22-carbon fatty acid also referred to as 4, 7, 10, 13, 16, 19-docosahexaenoic acid. In another embodiment, the omega-3 fatty acid is -linolenic acid (9, 12, 15-octadecatrienoic acid). In another embodiment, the omega-3 fatty acid is stearidonic acid (6, 9, 12, 15-octadecatraenoic acid). In another embodiment, the omega-3 fatty acid is eicosatrienoic acid (ETA; 11, 14, 17-eicosatrienoic acid). In another embodiment, the omega-3 fatty acid is eicsoatetraenoic acid (8, 11, 14, 17-eicosatetraenoic acid). In one embodiment, the omega-3 fatty acid is eicosapentaenoic acid (EPA; 5, 8, 11, 14, 17-eicosapentaenoic acid). In another embodiment, the omega-3 fatty acid is eicosahexaenoic acid (also referred to as 5, 7, 9, 11, 14, 17-eicosahexaenoic acid). In another embodiment, the omega-3 fatty acid is docosapentaenoic acid (DPA; 7, 10, 13, 16, 19-docosapenatenoic acid). In another embodiment, the omega-3 fatty acid is tetracosahexaenoic acid (6, 9, 12, 15, 18, 21-tetracosahexaenoic acid).

In other embodiments, the oil is a naturally-occurring oil comprising an omega-3 fatty acid. In more specific embodiments, the oil is selected from the group consisting of a fish oil, canola oil, flaxseed oil, algal oil and hemp seed oil. In more specific embodiments, the oil is a fish oil. Several types of fish oil have been tested in the compositions described herein and have all been found to work equally well.

Representative Specific Formulations

In still more specific embodiments, a liquid formulation utilized in the described method or composition comprises insulin, exenatide, Gelucire 44/14, EDTA, SBTI, aprotinin, and fish oil. In other embodiments, the liquid formulation consists essentially of insulin, exenatide, Gelucire 44/14, EDTA, SBTI, aprotinin, and fish oil. "Consists essentially of" for these purposes indicates that the liquid formulation does not contain any other components that appreciably affect its physiological characteristics. In other embodiments, the liquid formulation consists of insulin, exenatide, Gelucire 44/14, EDTA, SBTI, aprotinin, and fish oil. In other, even more specific embodiments, the amounts of insulin, exenatide, EDTA, SBTI, aprotinin, and fish oil per dosage form are 8-16 mg, 150-300 mcg, 100-200 mg, 50-100 mg, 20-30 mg, and 0.4-0.7 ml, respectively, and the amount of Gelucire 44/14 is 8-16%. In still more specific embodiments, the amounts of insulin, exenatide, EDTA, SBTI, aprotinin, and fish oil per dosage form are 8-16 mg, 150-300 mcg, 150 mg, 75 mg, 24 mg, and 0.5-0.7 ml, respectively, and the amount of Gelucire 44/14 is 8-16%. In other embodiments, the above composition further comprises a non-ionic detergent. In more specific embodiments, the non-ionic detergent is a polysorbate-based detergent. In even more specific embodiments, the polysorbate-based detergent is polysorbate 80. Preferably, the polysorbate 80 constitutes 3-10% weight/weight inclusive of the oil-based liquid formulation. In other embodiments, the above composition is coated by a coating that resists degradation in the stomach.

In still more specific embodiments, a liquid formulation utilized in the described method or composition comprises insulin, exenatide, a self-emulsifying component, EDTA, SBTI, aprotinin, and fish oil. In other embodiments, the liquid formulation consists essentially of insulin, exenatide, a self-emulsifying component, EDTA, SBTI, aprotinin, and fish oil. "Consists essentially of" for these purposes indicates that the liquid formulation does not contain any other components that appreciably affect its physiological characteristics. In other embodiments, the liquid formulation consists of insulin, exenatide, a self-emulsifying component, EDTA, SBTI, aprotinin, and fish oil. In other, even more specific embodiments, the amounts of insulin, exenatide, EDTA, SBTI, aprotinin, and fish oil per dosage form are 8-16 mg, 150-300 mcg, 100-200 mg, 50-100 mg, 20-30 mg, and 0.4-0.7 ml, respectively, and the amount of self-emulsifying component is 8-16%. In still more specific embodiments, the amounts of insulin, exenatide, EDTA, SBTI, aprotinin, and fish oil per dosage form are 8-16 mg, 150-300 mcg, 150 mg, 75 mg, 24 mg, and 0.5-0.7 ml, respectively, and the amount of self-emulsifying component is 8-16%. In other embodiments, the above composition further comprises a non-ionic detergent. In more specific embodiments, the non-ionic detergent is a polysorbate-based detergent. In even more specific embodiments, the polysorbate-based detergent is polysorbate 80. Preferably, the polysorbate 80 constitutes 3-10% weight/weight inclusive of the oil-based liquid formulation. In other embodiments, the above composition is coated by a coating that resists degradation in the stomach.

"Weight/weight" percentages referred to herein utilize the amount of oil base in the formulation, for example fish oil, as the denominator; thus, 60 mg of Gelucire in 500 mg fish oil is considered as 12% w/w, regardless of the weight of the other components. Similarly, 50 mg. Tween-80 mixed with 500 mg fish oil is considered as 10% Tween-80.

In other embodiments, a liquid formulation utilized in the described method or composition is water-free. If more than one liquid formulation is present, for example in a multi-component composition, each liquid formulation may be water-free. "Water-free" refers, in certain embodiments, to a formulation into which no aqueous components have been intentionally added. It does not preclude the presence of trace amounts of water that have been absorbed from the atmosphere into the components thereof. In another embodiment, the liquid formulation is free of aqueous components. If more than one liquid formulation is present, for example in a multi-component composition, each liquid formulation may be free of aqueous components. In yet other embodiments, one or more oils are the only liquid components of each of the one or more liquid formulations. In yet another embodiment, fish oil is the only liquid component of each of the one or more liquid formulations.

Coatings

Those of skill in the art will appreciate, given the present disclosure, that various pH-sensitive coatings may be utilized in the described methods and compositions. In certain embodiments, any coating that inhibits digestion of the composition in the stomach of a subject may be utilized. Typically, such coatings will not dissolve in human gastric juices within 2 hours, and will dissolve within 30 minutes in duodenal fluid.

In other embodiments, the coating comprises a biodegradable polysaccharide. In other embodiments, a hydrogel is utilized. In other embodiments, the coating comprises one of the following excipients: chitosan, an aquacoat ECD coating, an azo-crosslinked polymer, cellulose acetate phthalate, cellulose acetate trimellitate (CAT), cellulose acetate butyrate, hydroxypropylmethyl cellulose phthalate, or poly vinyl acetate phthalate.

In other embodiments, a timed-release system such as Pulsincap™ is utilized.

In preferred embodiments, the coated dosage forms described herein release the core (containing the oil-based formulation) when pH reaches the range found in the intestines, which is alkaline relative to that in the stomach. In more specific embodiments, the coating comprises a pH-sensitive polymer. In various embodiments, either mono-layer or multi-layer coatings may be utilized.

In one embodiment, the coating is an enteric coating. Methods for enteric coating are well known in the art (see, for example, Siepmann F et al 2005). In more specific embodiments, a Eudragit™ coating is utilized as the enteric coating. Eudragit™ coatings are acrylic polymers, the use of which is well known in the art.

In another embodiment, microencapsulation is used as a stomach-resistant coating in the compositions described herein. Methods for microencapsulation are well known in the art, and are described inter alia in United States Patent Application Publication No. 2011/0305768, which is incorporated by reference herein.

In other embodiments, the coating is a capsule. Gelatin capsules are most preferred. Methods for inserting an oil-based formulation into a gelatin capsule are well known in the art.

Pharmaceutical Compositions and Methods of Making Same

In another aspect a pharmaceutical composition described herein is provided for treating diabetes mellitus, for example Type 2 diabetes mellitus, in a human.

In yet another aspect, a use of a combination of ingredients described herein is provided in the preparation of a medicament for treating diabetes mellitus in a human.

Still another aspect provides a method for treating diabetes mellitus in a human, the method comprising the optional step of selecting a subject by diagnosing diabetes mellitus, followed by the step of administering to a subject in need of such treatment a pharmaceutical composition described herein, thereby treating diabetes mellitus in a human.

Still another aspect provides a method for treating a non-human animal with diabetes mellitus, the method comprising the step of administering to the non-human animal the oral pharmaceutical composition described herein, thereby treating the non-human animal with diabetes mellitus.

Still another aspect provides a method of manufacturing a pharmaceutical composition, comprising the steps of melting a waxy, self-emulsifying component; adding the molten component to fish oil, optionally cooling the resulting mixture; adding to the oil EDTA, SBTI in powder form, aprotinin in powder form, crystalline insulin, and exenatide in powder form, in some embodiments in the order listed; and mixing and homogenizing the resulting liquid, in some embodiments on a roller mill.

Yet another aspect provides a method of manufacturing a pharmaceutical composition, comprising the steps of melting a waxy, self-emulsifying component; adding the molten component to fish oil, optionally cooling the resulting mixture; adding to the oil EDTA, isolated BBI in powder form, isolated KTI3 in powder form, crystalline insulin, and exenatide in powder form, in some embodiments in the order listed; and mixing and homogenizing the resulting liquid, in some embodiments on a roller mill.

Yet another aspect provides a method of manufacturing a pharmaceutical composition, comprising the steps of melting a waxy, self-emulsifying component; adding the molten component to fish oil, optionally cooling the resulting mixture; adding to the oil EDTA, isolated KTI3 in powder form, aprotinin in powder form, crystalline insulin, and exenatide in powder form, in some embodiments in the order listed; and mixing and homogenizing the resulting liquid, in some embodiments on a roller mill.

Yet another aspect provides a use of a combination of ingredients described hereinabove in the preparation of a medicament for treating unstable diabetes, also known as glycemic lability (Ryan et al, 2004) in a human. Yet another aspect provides a method for treating unstable diabetes, the method comprising the step of administering to a subject in need of such treatment a pharmaceutical composition described hereinabove, thereby treating unstable diabetes.

Provided in another embodiment is a use of a combination of ingredients described hereinabove in the preparation of a medicament for treating an elevated fasting blood glucose level in a human. Provided in another embodiment is a method for treating an elevated fasting blood glucose level, the method comprising the step of administering to a subject in need of such treatment a pharmaceutical composition described hereinabove, thereby treating an elevated fasting blood glucose. In certain preferred embodiments, the subject is a human subject. In various embodiments, elevated fasting blood glucose is considered to exist in a subject having a glycated hemoglobin [HgA1c] level of 8-10%, or a fasting plasma sugar level from 100 to 125 mg/dL, or 5.6 to 6.9 mmol/L.

Provided herein, in another embodiment, is a method of treating elevated total cholesterol, the method comprising the step of administering to a subject in need of such treatment a pharmaceutical composition described hereinabove, thereby treating elevated total cholesterol.

Another aspect provides a method of treating hypertriglyceridemia, the method comprising the step of administering to a subject in need of such treatment a pharmaceutical composition described hereinabove, thereby treating hypertriglyceridemia.

Another aspect provides a method of treating elevated serum apolipoprotein B (ApoB), the method comprising the step of administering to a subject in need of such treatment a pharmaceutical composition described hereinabove.

Another aspect provides a method of treating elevated total cholesterol/HDL ratio, the method comprising the step of administering to a subject in need of such treatment a pharmaceutical composition described hereinabove.

Another aspect provides a method of treating an elevated apolipoprotein B/apolipoprotein A1 ratio, the method comprising the step of administering to a subject in need of such treatment a pharmaceutical composition described hereinabove, thereby treating an elevated apolipoprotein B/apolipoprotein A1 ratio.

Methods for measuring each of the aforementioned lipid parameters are well known to those skilled in the art. Exemplary methods are described inter alia in Chiquette E et al and Martinez-Colubi M et al.

Another aspect provides a method of treating an impaired insulin-induced enhancement of vasodilator responses in a subject with metabolic syndrome, the method comprising the step of administering to a subject in need of such treatment a pharmaceutical composition described hereinabove, thereby treating an impaired insulin-induced enhancement of vasodilator responses in a subject with metabolic syndrome. Methods for measuring insulin-induced vasodilator responses are known in the art, and include, for example, measuring blood flow responses (for example in the forearm) to acetylcholine (ACh) and sodium nitroprusside (SNP) (Tesauro et al).

Metabolic syndrome is considered to be present if at least three of the following factors are present:
1. A large waistline (abdominal obesity).
2. A high triglyceride level (or a high triglyceride level in the absence of medicine to treat high triglycerides).
3. A low HDL cholesterol level (or low HDL cholesterol in the absence of medicine to treat low HDL cholesterol).
4. Hypertension (or hypertension in the absence of medicine to treat hypertension.
5. High fasting blood sugar (or high fasting blood sugar in the absence of medicine to treat high fasting blood sugar).

Another aspect provides a method of treating non-alcoholic steatohepatitis in a subject with metabolic syndrome, the method comprising the step of administering to a subject in need of such treatment a pharmaceutical composition described herein, thereby treating non-alcoholic steatohepatitis in a subject with metabolic syndrome. Methods of diagnosing and measuring non-alcoholic steatohepatitis are well known in the art, and include, for example, measuring plasma aspartate transaminase (AST) levels, plasma alanine transaminase (ALT) levels, hepatic mRNA levels of genes involved in lipogenesis, and diacylglycerol acyltransferase-2 (DGAT2) levels in the liver (Miyashita T et al).

Another aspect provides a method of treating elevated total cholesterol, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating elevated total cholesterol, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating hypertriglyceridemia, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating hypertriglyceridemia, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating elevated serum ApoB, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating elevated serum ApoB, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating an elevated total cholesterol/HDL ratio, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating an elevated total cholesterol/HDL ratio, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating an elevated apolipoprotein B/apolipoprotein A1 ratio, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating an elevated apolipoprotein B/apolipoprotein A1 ratio, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating an impaired insulin-induced enhancement of vasodilator responses in a subject with metabolic syndrome, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach.

Another aspect provides a method of treating an impaired insulin-induced enhancement of vasodilator responses in a subject with metabolic syndrome, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Another aspect provides a method of treating non-alcoholic steatohepatitis in a subject with metabolic syndrome, the method comprising the step of administering to a subject in need of such treatment an oral, oil-based liquid formulation, the oil-based liquid formulation comprising an insulin, one or, in another embodiment more than one, trypsin inhibitor, and a chelator of divalent cations, wherein the oil-based liquid formulation is surrounded by a coating or capsule that resists degradation in the stomach. Another aspect provides a method of treating non-alcoholic steatohepatitis in a subject with metabolic syndrome, the method comprising the step of administering to a subject in need of such treatment an oral, oil-based liquid formulation, the oil-based liquid formulation comprising a GLP-1 analogue, one or, in another embodiment more than one, trypsin inhibitor, and a chelator of divalent cations, wherein the oil-based liquid formulation is surrounded by a coating or capsule that resists degradation in the stomach. The oil, insulin, GLP-1 analogue, trypsin inhibitor(s), chelator, coating, and other optional ingredients of the above compositions may be any described herein; each alternative may be combined freely to form discrete embodiments of the invention disclosed herein.

Wherever alternatives for single separable features such as, for example, a insulin protein or dosage thereof, a GLP-1 analogue of dosage thereof, a protease inhibitor, a chelator, an emulsifier, or a coating are laid out herein as "embodiments", it is to be understood that such alternatives may be combined freely to form discrete embodiments of the invention disclosed herein.

With respect to the jurisdictions allowing it, all patents, patent applications, and publications mentioned herein, both supra and infra, are incorporated herein by reference.

The invention is further illustrated by the following examples and the figures, from which further embodiments and advantages can be drawn. These examples are meant to illustrate the invention but not to limit its scope.

EXPERIMENTAL DETAILS SECTION

Example 1

Identification of Effective Emulsifiers for Homogenous Therapeutic Protein/Fish Oil Preparations Previous formulations of insulin in fish oil were found to exhibit precipitation with the passage of time; they were thus inconvenient for large-scale pharmaceutical dosage form preparation. New formulations containing 3.375 g. SBTI per 22.5 g. of fish oil and containing the following emulsifiers were tested: lecithin (trial sequence 1), Polysorbate 80 (Tween-80) (sequence 2), or Gelucire® 44/14 (sequence 3), alone or in combination with each other or glycerol monostearate (GMS) (FIG. 1). Subsequently, the most promising formulations (indicated with an asterisk) were produced again by melting the Gelucire® (which was a waxy solid as ambient temperature), then adding it to the fish oil. After cooling this mixture, the solid components were added in powder form in the following order: EDTA, SBTI, aprotinin, and insulin; and the resulting liquid was mixed and homogenized on a roller mill.

Example 2

In Vivo Testing of Various Emulsifier Formulations

Materials and Experimental Methods
Formulations

The formulations tested in Experiments 2A and 2B are shown below in Table 1. Percentages of emulsifiers are expressed as weight/weight with respect to the weight of the liquids present.

TABLE 1

| Formulation name | Emulsifiers | Other ingredients |
|---|---|---|
| Experiment 2A | | |
| GMS 2% | GMS 2% only | 3.375 g. SBTI, 6.75 mg EDTA, 1.08 mg aprotinin, 0.39 mg. human insulin, 22.5 g. of fish oil |
| 2%-2% | 2% GMS, 2% lecithin | Same as above. |
| 2%-10% | 2% GMS, 10% lecithin | Same as above. |
| 10% lec. | 10% lecithin only | Same as above. |
| Experiment 2B | | |
| A | 5% lecithin, 2% GMS | Same as above. |
| B | 3% lecithin, 12% Gelucire 44/14 | Same as above. |
| C | 6% lecithin, 12% Gelucire 44/14 | Same as above. |
| D | 5% Tween-80, 12% Gelucire 44/14 | Same as above. |
| E | 10% Tween-80, 12% Gelucire 44/14 | Same as above. |
| F | 12% Gelucire 44/14 only | Same as above. |

Husbandry

Animal health: Only healthy pigs, as certified by a clinical veterinarian, were used for the study. Housing: Solitary when with CVC and grouped at other times. Bedding: Concrete+woodchips. Illumination: 12-12 h light cycle. Temperature: 19-25° C.

Identification

Each animal was uniquely identified via ear tags.

Experimental Design

Animals were deprived of food 24-36 hours prior to testing. Access to water was ad libitum.

Animals were anesthetized with 20 mg/kg ketamine+2 mg/kg xylazine. Fasting and anesthetized pigs were positioned on their left side before liquid formulations were administered under endoscopic guidance, directly to the duodenum. After injection of the formulation, 1 mL fish oil was injected, followed by 10 mL air, to flush the apparatus, thereby ensuring administration of the entire formulation. Pigs were then returned to their pens to allow for full recovery from the anesthetic treatment, which required 10-15 min. Blood samples (0.5 mL of which were analyzed) were periodically drawn from the central line catheter (CVC) over the ensuing 240-min monitoring period. Blood glucose concentrations were determined from each sample, at each time point. Piglets were intravenously treated with gentamycin (100 mg/10 kg) after every experiment day to avoid infection. In cases where glucose concentrations dropped below 30 mg/dL, piglets were served commercial pig chow, and glucose concentrations were monitored for an additional 30 minutes thereafter.

A washout period of at least 2 days was enforced between test days.

Results 10 insulin-fish oil formulations with different emulsifiers were tested for in-vivo activity on blood glucose levels in 2 separate experiments. Results are described below.

TABLE 2

Results of Experiment 2A. The three numbers in each box indicate baseline value, lowest value, and end (20 mg/dL). "Low" indicates a value of less than 20 mg/dL.

| Formulation | Pig 1 | Pig2 | Pig3 | Pig4 | Pig 5 (stoma) | Score |
|---|---|---|---|---|---|---|
| GMS 2% | 78 → 48 → 65 | 72 →low → low | 63 →23 → 28 | 67 → 32 → 60 | 55 → 21 → 58 | 3 |
| 2% GMS, 2% lecithin | 82 → Low → 65 | 78 →45 → 76 | 85 →30 → 68 | 78 → 23 → 61 | | 2 |
| 2% GMS, 10% lecithin | 76 → Low → 77 | 76 →low → 21 | 76 →low → low | 74 → low → 70 | | 4 |
| 10% lecithin | 51 → 63 → 71 | 50 →low → low | 57 →low → low | 61 → low → low | | 5 |

The results of Experiment 2B are indicated in FIG. 2.

Example 3

Figure 3:
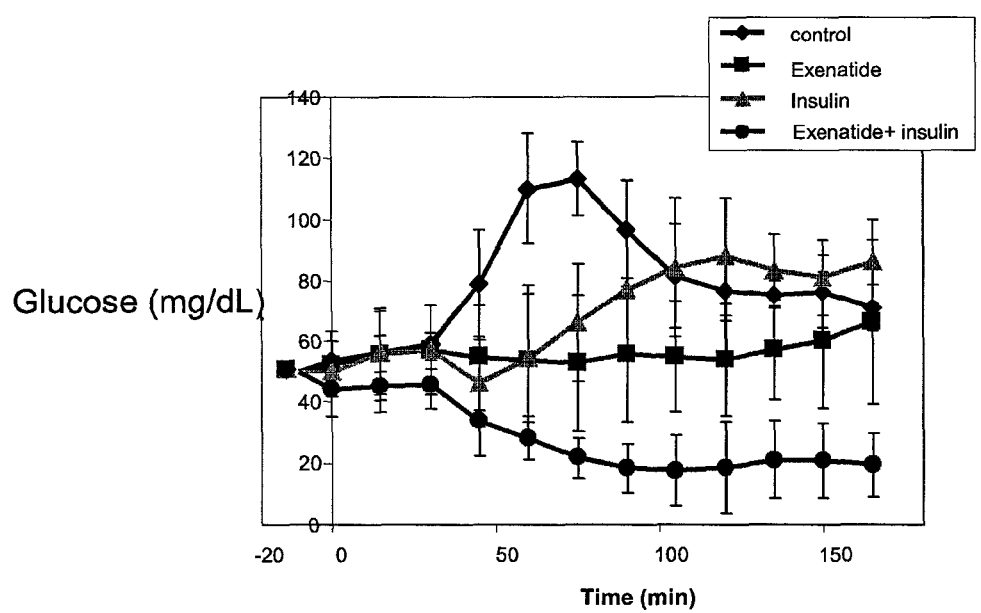
FIG. 3. Blood glucose profiles following oral exenatide and oral insulin administration to pigs. Fasting, commercial pigs were treated with 150 mcg. exenatide, 8 mg. insulin, or the combination thereof, 30 minutes before caloric intake. 1-mL blood samples were periodically drawn throughout the 180-minute observation period to determine glucose concentrations.

An Oral Insulin/Oral Exenatide Combination Sharply Reduces Blood Glucose Levels and Prevents Postprandial Glucose Excursions Materials and Experimental Methods
Animals
Healthy 25-30 kg, 3-4 month-old pigs were used.
Experimental Design
Pigs were deprived of food for 24-36 hours before the start of the study. CVCs were replaced every five days, unless circumstances required earlier replacement. Animals were anesthetized by isoflurane administration through a mask before tracheal intubation and respirator hook-up (2 L $O_2$ per minute and 3-5% isoflurane, when required), then were positioned on their left side and capsules were administered directly into the duodenum, using an endoscopic basket under endoscopic guidance. When both oral insulin and oral exenatide were administered, oral exenatide was delivered first, followed by oral insulin within 2-10 minutes. Pigs were returned to their pens to allow for full recovery from the anesthetic treatment and 30 minutes after capsule administration were given 10 g/kg piglet commercial milk powder (Denkapig Premium (Denkavit) prepared in an equal volume of water. Meals were typically consumed within 7-15 minutes. Blood samples were periodically drawn from the CVC for glucose concentration testing over the ensuing 240-min monitoring period. Piglets were intravenously treated with gentamycin (100 mg/10 kg) after every experiment day to avoid infection. In cases where glucose concentrations dropped below 30 mg/dL, piglets were served commercial pig chowder and glucose concentrations were monitored for an additional 30 minutes thereafter. Control pigs were untreated. Three pigs were used, each of whom received each formulation a number of times. The number of tests were n=5 for oral insulin, n=5 for oral exenatide, n=7 for the combination, and n=6 for the control.
Formulations
The oral insulin formulation contained 8 mg insulin, 12% Gelucire 44/14, 150 mg EDTA, 75 mg SBTI, and 24 mg aprotinin in 0.5-0.7 mL fish oil. The liquid was coated by a soft-gel, enteric-coated capsule. The dosage form was manufactured by Swiss Caps AG.
The oral exenatide formulation contained 150 microgram (mcg) exenatide, 150 mg EDTA, 75 mg SBTI, and 24 mg aprotinin in 0.5-0.7 mL fish oil. The liquid was coated by a soft-gel, enteric-coated capsule. The dosage form was manufactured by Swiss Caps AG.
Statistical Analysis
p-values were calculated using a paired, one-tailed t-test.
Results
As expected, placebo-treated pigs experienced glucose excursions following caloric intake. Pigs treated with oral exenatide 30 minutes before caloric intake completely avoided the glucose excursions throughout the 150 minutes following caloric intake (FIG. 3). Oral insulin also curbed glucose excursions, but did not fully prevent a rise in blood glucose concentrations throughout the entire monitoring period. A sharply greater effect was observed upon combined treatment with oral exenatide and oral insulin. In addition to fully preventing glucose excursions, the combined treatment reduced glucose concentrations to a low of more than 50% below baseline values during the entire period from the 70-minute timepoint until the end of the 180-minute monitoring session. The difference in blood glucose levels was statistically significant compared to no treatment or treatment with insulin or exenatide alone (p-values: combination vs. control: $5.3 \times 10^{-5}$; combination vs. oral insulin: 0.00015, and combination vs. oral exenatide: $1.6 \times 10^{-5}$).

Example 4

Testing of an Oral Insulin/Oral Exenatide Combination in Human Subjects

Volunteers, either diabetic or non-diabetic, are administered prior to a meal one or more dosage forms having a pH-sensitive coating or capsule containing a liquid formulation containing one or more protease inhibitors, EDTA, insulin and exenatide. One representative formulation is 50-200 mg. per capsule SBTI; 20-30 mg. per capsule Aprotinin; 75-200 mg EDTA; 8-32 mg. per capsule insulin; 150-600 mcg. per capsule exenatide; and 0.5-0.7 ml fish oil, optionally with an emulsifier (e.g. 8-20% Gelucire® 44/14). In other experiments, subjects are administered two encapsulated liquid formulations, one containing protease inhibitor(s), EDTA, and insulin, and the other containing protease inhibitor(s), EDTA, and exenatide. One representative formulation is a first capsule containing one or more protease inhibitors, EDTA, and insulin in a liquid formulation, optionally with an emulsifier (e.g. Gelucire® 44/14), together with a second capsule containing protease inhibitors, emulsifier, EDTA, and exenatide in a liquid formulation, optionally with an emulsifier (e.g. Gelucire® 44/14).

Subjects are challenged with a 75 g oral glucose load after capsule administration (for example 30-60 minutes later) and relevant physiological parameters are subsequently monitored by collection of blood samples.

The following protocol is an exemplary protocol that may be used. Those skilled in the art will appreciate that nonessential details of the protocol may be modified without compromising its ability to provide the desired information.
Overview
Stage I:
Stage I consists of two segments. Segment 1 will assess the safety, tolerability and the pharmacokinetics/pharmacodynamics (PK/PD) of escalating doses of oral exenatide in eight (8) healthy volunteers. In the first segment, the two lower doses of oral exenatide (150 and 300 μg exenatide) will be randomly tested among all healthy, fasting subjects. If deemed safe, further dose escalation (450 and 600 μg exenatide) will be authorized in Segment 2. The highest tolerable dose will then be administered to the subjects 60 minutes before a standard meal (Visit 5).
Stage II:
This stage will assess the T2DM patient response to escalating doses of exenatide when delivered 60 min before a standard meal. Placebo controls will be included in the study, as will treatment with an active control of Byetta® (5 μg) subcutaneously delivered 30 min before a standard meal. In addition, the T2DM subjects will be treated with an oral insulin capsule containing 16 mg of insulin and with a combination of oral insulin/oral exenatide, at two independent study visits, 60 minutes before a standard meal.

In addition to exenatide and/or insulin, all formulations contain 75 mg SBTI, 24 mg aprotinin, and 150 mg EDTA, all in fish oil, in enteric-coated capsules.

Interpretation:

The AUC of glucose reductions and insulin excursion will be calculated and compared between the different treatments.

Study Population:

Healthy: Male, healthy individuals.

T2DM:

The presence of T2DM is determined by WHO criteria. Subjects may be of either gender, between the ages of 18 and 60, with stable glycemic control, optionally on oral antidiabetes medication (e.g. metformin and/or TZDs), and not pregnant or breastfeeding. Subjects will continue their regular medications and dosing regimen up to the night prior to the study. Patients will resume their regular medication after completing each study session (same day). Other than diabetes, subjects should be in general good health, with stable liver enzyme levels (below 2× the upper normal range).

Procedures

Stage I:

Segment I of the treatment phase will consist of two visits, evaluating 150 μg and 300 μg oral exenatide versus placebo treatment in healthy subjects, administered in the morning after an 8-hr fast. Further dose escalation to Segment II will be authorized if no serious side effects and safety and tolerability are demonstrated. In Segment II, fasting subjects will be administered 450 and/or 600 μg oral exenatide and/or placebo to fasting individuals (Appendix 1). The highest tolerable dose will then be delivered 60 minutes before intake of a standard meal.

Each dosing will be followed by at least a 72-hour washout period.

Screening Phase:

The following evaluations may be performed:
Medical history
Physical examination
Medication history
ECG
Vital signs (blood pressure, heart rate). Vital signs will be measured in the sitting position after at least 5 minutes of rest.
Clinical laboratory evaluations (chemistry, hematology, HgA1C)

Treatment Phase:

1. Blood samples will be obtained at −45, −30, −15, 0, 15, 30, 45, 60, 75, 90, 105, 120, 135, 150 min, where time=0 is the time at which the capsule is ingested, and tested for glucose, insulin, c-peptide, as well as GLP-1 analogue content.
2. A standard meal will be served 60 minutes after oral exenatide administration to healthy patients at visit 5 only.
3. Gastrointestinal symptoms may be assessed.

Stage II:

300 and 600 micrograms exenatide, or the two highest tolerable doses determined in Stage I, will be administered in parallel and in combination with 16 mg insulin, for example as 16 mg combined with 300 microgram, 60 minutes before a standard meal. On study visits where an injection of Byetta® (5 μg) is administered, a meal will be served 30 minutes after dosing.

Screening Phase:
Same as for Stage I.

Treatment Phase:

1. Blood samples will be drawn at −15, 0, 15, 30, 45, 60, 75, 90, 105, 120, 135, 150, and 240 min, where time=0 is the time at which the capsule is ingested, and tested for glucose, insulin, c-peptide, as well as GLP-1 analogue levels ($C_{max}$, $T_{max}$ and/or AUC)

2. A standard meal will be served 60 minutes after oral dosing or 30 minutes after subcutaneous administration of Byetta®.
3. Gastrointestinal symptoms may be assessed.

Treatments (delivered in a randomized order):
a. 300 or 600 mcg oral exenatide, or placebo, or 5 mcg subcutaneous exenatide
b. 300 or 600 mcg oral exenatide, or placebo, or 5 mcg subcutaneous exenatide
c. 300 or 600 mcg oral exenatide, or placebo, or 5 mcg subcutaneous exenatide
d. 16 mg oral insulin
e. 300 mcg oral exenatide+16 mg oral insulin.

Safety Evaluations:

Adverse events will be collected throughout the study beginning from the time the subject signs the consent form until the end of study evaluations Concomitant medications/therapies will be recorded throughout the duration of study, beginning from the time the subject signs the informed consent.

Vital signs (blood pressure, heart rate) will be measured in the sitting position after at least 5 minutes of rest at the following times:
Screening
Approximately 20 minutes prior to study drug administration
Approximately 1 and 2.5 hours post study drug administration Clinical laboratory evaluations (chemistry, hematology) will be performed at screening and at end of study or early discontinuation.

Physical examinations at screening and end of study or early discontinuation.

Electrocardiograms (ECG) at screening. An ECG will be performed at end of study or early discontinuation, only if the investigator deems it necessary.

Example 5

Testing of an Oral Insulin/Oral Exenatide Combination in Treatment of Unstable Diabetes Subjects with elevated fasting glucose levels (for example, subjects having a glycated hemoglobin [HgA1c] level of 8-10%, or a fasting plasma sugar level from 100 to 125 mg/dL or 5.6 to 6.9 mmol/L).) are monitored for several days using a blinded continuous glucose monitor (CGM) to establish a baseline. During several subsequent days, they are administered a formulation described herein, optionally prior to meals. Blinded CGM is performed to determine the efficacy of the formulations.

In the claims, the word "comprise", and variations thereof such as "comprises", "comprising", and the like indicate that the components listed are included, but not generally to the exclusion of other components.

REFERENCES

Chiquette E et al. Treatment with exenatide once weekly or twice daily for 30 weeks is associated with changes in several cardiovascular risk markers. Vasc Health Risk Manag. 2012; 8:621-9.

Eldor R, Kidron M, Arbit E. A single-bling, two-period study to assess the safety and pharmacodynamics of an orally delivered GLP-1 analog (exenatide) in healthy subjects. American Diabetes Association 70th Annual Scientific Sessions, Jun. 25-29, 2010A, Orlando, Fla.

Eldor R, Kidron M, Arbit E. Open-label study to assess the safety and pharmacodynamics of five oral insulin formulations in healthy subjects. *Diabetes Obes Metab.* March 2010B; 12(3):219-223.

Eldor R, Kidron M, Greenberg-Shushlav Y, Arbit E. Novel glucagon-like peptide-1 analog delivered orally reduces postprandial glucose excursions in porcine and canine models. *J Diabetes Sci Technol.* 2010C; 4(6):1516-1523.

Kidron M, Dinh S, Menachem Y, et al. A novel per-oral insulin formulation: proof of concept study in non-diabetic subjects. *Diabet Med.* April 2004; 21(4):354-357.

Martinez-Colubi M et al, Switching to darunavir/ritonavir monotherapy (DRV/r mx): effect on kidney function and lipid profile. J Int AIDS Soc. 2012 Nov. 11; 15(6):18348. doi: 10.7448/IAS.15.6.18348.

Miyashita T et al, Hepatoprotective effect of tamoxifen on steatosis and non-alcoholic steatohepatitis in mouse models. J Toxicol Sci. 2012; 37(5):931-42

Ryan E A, Shandro T, Green K et al. Assessment of the severity of hypoglycemia and glycemic lability in type 1 diabetic subjects undergoing islet transplantation. *Diabetes.* 2004 April; 53(4):955-62.

Siepmann F, Siepmann J et al, Blends of aqueous polymer dispersions used for pellet coating: importance of the particle size. J Control Release 2005; 105(3): 226-39.

Sun J., Rose J. B., Bird P. (1995) J. Biol. Chem. 270, 16089-16096.

Nissan A, Ziv E, Kidron M, et al. Intestinal absorption of low molecular weight heparin in animals and human subjects. *Haemostasis.* September-October 2000; 30(5): 225-232.

Sprecher C A, Morgenstern K A, Mathewes S, Dahlen J R, Schrader S K, Foster D C, Kisiel W. J Biol. Chem. 1995 Dec. 15; 270(50):29854-61.

Tesauro et al. Effects of GLP-1 on Forearm Vasodilator Function and Glucose Disposal During Hyperinsulinemia in the Metabolic Syndrome. Diabetes Care. 2012 Oct. 15.

Ziv E, Kidron M, Raz I, et al. Oral administration of insulin in solid form to nondiabetic and diabetic dogs. *J Pharm Sci.* June 1994; 83(6):792-794.

---

The invention claimed is:

1. An oral pharmaceutical composition, comprising an oil-based liquid formulation, said oral pharmaceutical composition comprising an insulin and exenatide, a trypsin inhibitor, and a chelator of divalent cations, wherein said oil-based liquid formulation is surrounded by a coating that resists degradation in the stomach,
   wherein said insulin is present at an amount of between 6-14 milligrams inclusive and said exenatide is present in an amount of between 100-500 micrograms inclusive for an adult patient or a corresponding amount per body weight for a pediatric patient,
and
   wherein administration of the composition to a subject prior to caloric ingestion lengthens the time that the subject's blood sugar is lowered, after caloric ingestion, to a level that is lower than the level that results if the subject was administered a control composition that is the same except that it lacks the insulin, the exenatide, or both.

2. An oral pharmaceutical composition, comprising a combination of i). a first oil-based liquid formulation, said first oil-based liquid formulation comprising an insulin, a trypsin inhibitor, and a chelator of divalent cations; and ii). a second oil-based liquid formulation, said second oil-based liquid formulation comprising exenatide, a trypsin inhibitor, and a chelator of divalent cations, wherein each of said first oil-based liquid formulation and said second oil-based liquid formulation is surrounded by a coating that resists degradation in the stomach,
   wherein said insulin is present at an amount of between 6-14 milligrams inclusive and said exenatide is present in an amount of between 100-500 micrograms inclusive for an adult patient or a corresponding amount per body weight for a pediatric patient,
and
   wherein administration of the composition to a subject prior to caloric ingestion lengthens the time that the subject's blood sugar is lowered, after caloric ingestion, to a level that is lower than the level that results if the subject was administered a control composition that is the same except that it lacks the insulin, the exenatide, or both.

3. The oral pharmaceutical composition of claim 2, wherein said oil-based liquid formulation, or both said first oil-based liquid formulation and said second oil-based liquid formulation, further comprises a component provided as a mixture of (a) a monoacylglycerol, a diacylglycerol, a triacylglycerol, or a mixture thereof; and (b) a polyethylene glycol (PEG) ester of a fatty acid.

4. The oral pharmaceutical composition of claim 1, wherein said oil-based liquid formulation further comprises a self-emulsifying component.

5. The oral pharmaceutical composition of claim 1, wherein said insulin is present in an amount between 4-12 mg inclusive for an adult patient or a corresponding amount per body weight for a pediatric patient.

6. The oral pharmaceutical composition of claim 5, wherein said exenatide is present in an amount between 100-300 micrograms inclusive for an adult patient or a corresponding amount per body weight for a pediatric patient.

7. The oral pharmaceutical composition of claim 1, wherein said exenatide is present in an amount between 100-300 micrograms inclusive for an adult patient or a corresponding amount per body weight for a pediatric patient.

8. The oral pharmaceutical composition of claim wherein said trypsin inhibitor is selected from the group consisting of soybean trypsin inhibitor (SBTI), Bowman-Birk inhibitor (BBI), and aprotinin.

9. The oral pharmaceutical composition of claim 1, further comprising a second trypsin inhibitor.

10. The oral pharmaceutical composition of claim 9, wherein said first and second trypsin inhibitors are (i) SBTI and (ii) aprotinin; or said first and second trypsin inhibitors are (i) isolated KTI3 and (ii) isolated BB1.

11. The oral pharmaceutical composition of claim wherein said chelator is EDTA.

12. The oral pharmaceutical composition of claim 1, wherein said oil is fish oil.

13. The oral pharmaceutical composition of claim 1, wherein said oil-based liquid formulation is water-free.

14. The oral pharmaceutical composition of claim 9, wherein the composition does not comprise both SBTI and aprotinin.

15. The oral pharmaceutical composition of claim 1, wherein said coating is a pH-sensitive capsule.

16. The oral pharmaceutical composition of claim 1, wherein administration of the composition reduced postprandial glucose excursion in a human having Type 2 diabetes mellitus.

17. The oral pharmaceutical composition of claim 16, wherein said insulin is present in an amount between 4-12 mg inclusive, and said exenatide is present in an amount between 100-300 micrograms inclusive for an adult patient or a corresponding amount per body weight for a pediatric patient.

18. A method for treating a human with Type 2 diabetes mellitus, said method comprising the steps of selecting a subject diagnosed with Type 2 diabetes mellitus, and administering said subject the oral pharmaceutical composition of claim 1, thereby treating a human with Type 2 diabetes mellitus.

19. A method for treating a non-human animal with diabetes mellitus, said method comprising the step of administering to said non-human animal the oral pharmaceutical composition of claim 1, thereby treating a non-human animal with diabetes mellitus.

20. A method for reducing postprandial glucose excursion in a human with Type 2 diabetes mellitus, said method comprising the steps of selecting a subject diagnosed with Type 2 diabetes mellitus, and administering said subject oral pharmaceutical composition of claim 1, thereby reducing postprandial glucose excursion in a human with Type 2 diabetes mellitus.

21. A method for reducing postprandial glucose excursion in a non-human animal with diabetes mellitus, said method comprising the step of administering to said non-human animal the oral pharmaceutical composition of claim 1, thereby reducing postprandial glucose excursion in a non-human animal with diabetes mellitus.

22. A method for treating an elevated fasting blood glucose level in a human, said method comprising administering said subject oral pharmaceutical composition of claim 1.

23. A method for treating an elevated fasting blood glucose level in a non-human animal, said method comprising administering said subject oral pharmaceutical composition of claim 1.

* * * * *

SEQUENCE LISTING

```
<160> NUMBER OF SEQ ID NOS: 4

<210> SEQ ID NO 1
<211> LENGTH: 100
<212> TYPE: PRT
<213> ORGANISM: Bos taurus

<400> SEQUENCE: 1

Met Lys Met Ser Arg Leu Cys Leu Ser Val Ala Leu Leu Val Leu Leu
1               5                   10                  15

Gly Thr Leu Ala Ala Ser Thr Pro Gly Cys Asp Thr Ser Asn Gln Ala
            20                  25                  30

Lys Ala Gln Arg Pro Asp Phe Cys Leu Glu Pro Pro Tyr Thr Gly Pro
        35                  40                  45

Cys Lys Ala Arg Ile Ile Arg Tyr Phe Tyr Asn Ala Lys Ala Gly Leu
    50                  55                  60

Cys Gln Thr Phe Val Tyr Gly Gly Cys Arg Ala Lys Arg Asn Asn Phe
65                  70                  75                  80

Lys Ser Ala Glu Asp Cys Met Arg Thr Cys Gly Gly Ala Ile Gly Pro
                85                  90                  95

Trp Glu Asn Leu
            100

<210> SEQ ID NO 2
<211> LENGTH: 110
<212> TYPE: PRT
<213> ORGANISM: Glycine max

<400> SEQUENCE: 2

Met Val Val Leu Lys Val Cys Leu Val Leu Leu Phe Leu Val Gly Gly
1               5                   10                  15

Thr Thr Ser Ala Asn Leu Arg Leu Ser Lys Leu Gly Leu Leu Met Lys
            20                  25                  30

Ser Asp His Gln His Ser Asn Asp Glu Ser Ser Lys Pro Cys Cys
        35                  40                  45

Asp Gln Cys Ala Cys Thr Lys Ser Asn Pro Pro Gln Cys Arg Cys Ser
    50                  55                  60

Asp Met Arg Leu Asn Ser Cys His Ser Ala Cys Lys Ser Cys Ile Cys
65                  70                  75                  80
```

```
Ala Leu Ser Tyr Pro Ala Gln Cys Phe Cys Val Asp Ile Thr Asp Phe
                85                  90                  95
Cys Tyr Glu Pro Cys Lys Pro Ser Glu Asp Asp Lys Glu Asn
            100                 105                 110

<210> SEQ ID NO 3
<211> LENGTH: 216
<212> TYPE: PRT
<213> ORGANISM: Glycine max

<400> SEQUENCE: 3

Met Lys Ser Thr Ile Phe Phe Leu Phe Leu Phe Cys Ala Phe Thr Thr
1               5                   10                  15

Ser Tyr Leu Pro Ser Ala Ile Ala Asp Phe Val Leu Asp Asn Glu Gly
                20                  25                  30

Asn Pro Leu Glu Asn Gly Gly Thr Tyr Tyr Ile Leu Ser Asp Ile Thr
            35                  40                  45

Ala Phe Gly Gly Ile Arg Ala Ala Pro Thr Gly Asn Glu Arg Cys Pro
        50                  55                  60

Leu Thr Val Val Gln Ser Arg Asn Glu Leu Asp Lys Gly Ile Gly Thr
65                  70                  75                  80

Ile Ile Ser Ser Pro Tyr Arg Ile Arg Phe Ile Ala Glu Gly His Pro
                85                  90                  95

Leu Ser Leu Lys Phe Asp Ser Phe Ala Val Ile Met Leu Cys Val Gly
                100                 105                 110

Ile Pro Thr Glu Trp Ser Val Val Glu Asp Leu Pro Glu Gly Pro Ala
            115                 120                 125

Val Lys Ile Gly Glu Asn Lys Asp Ala Met Asp Gly Trp Phe Arg Leu
        130                 135                 140

Glu Arg Val Ser Asp Asp Glu Phe Asn Asn Tyr Lys Leu Val Phe Cys
145                 150                 155                 160

Pro Gln Gln Ala Glu Asp Asp Lys Cys Gly Asp Ile Gly Ile Ser Ile
                165                 170                 175

Asp His Asp Asp Gly Thr Arg Arg Leu Val Val Ser Lys Asn Lys Pro
            180                 185                 190

Leu Val Val Gln Phe Gln Lys Leu Asp Lys Glu Ser Leu Ala Lys Lys
        195                 200                 205

Asn His Gly Leu Ser Arg Ser Glu
    210                 215

<210> SEQ ID NO 4
<211> LENGTH: 39
<212> TYPE: PRT
<213> ORGANISM: Heloderma suspectum
<220> FEATURE:
<221> NAME/KEY: misc_feature
<222> LOCATION: (39)..(39)
<223> OTHER INFORMATION: residue is amidated on C-terminus

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35
```